United States Patent [19]

Leedham et al.

[11] Patent Number: 5,504,195
[45] Date of Patent: Apr. 2, 1996

[54] RARE EARTH COMPOUNDS AND THEIR PREPARATION

[75] Inventors: Timothy J. Leedham, Milton; Simon R. Drake, London, both of United Kingdom

[73] Assignee: Rhone-Poulenc Chimie, Courbevoie, France

[21] Appl. No.: 185,379

[22] Filed: Jan. 24, 1994

[30] Foreign Application Priority Data

Jan. 22, 1993 [GB] United Kingdom ............... 9301242

[51] Int. Cl.⁶ ........................................ C07F 5/00
[52] U.S. Cl. ............................... 534/15; 505/100
[58] Field of Search ...................... 534/15; 505/100

[56] References Cited

U.S. PATENT DOCUMENTS

| | | | |
|---|---|---|---|
| 3,254,103 | 5/1966 | Melby et al. | 260/429.2 |
| 5,140,003 | 8/1992 | Mueller | 505/100 |
| 5,225,561 | 7/1993 | Kirlin et al. | 546/256 |
| 5,264,634 | 11/1993 | Becker et al. | 568/413 |
| 5,280,012 | 1/1994 | Kirlin et al. | 505/100 |

FOREIGN PATENT DOCUMENTS

WO89/07666  8/1989  WIPO.

OTHER PUBLICATIONS

A. M. Grotens et al., "Lanthanide Induced Contact Shifts In Polyglycoldimethylethers, IV Chemical Exchange", Tetrahedron Letters, No. 17, 1973, pp. 1467–1470.

Simon R. Drake et al., "Lanthanide β–Diketonate Glyme Complexes Exhibiting Unusual Co–Ordination Modes", Journal of the Chemical Society Dalton Translations, No. 15, 1993, pp. 2379–2386.

P. J. Nigrey, "Thin–Film Superconductor Manufacture", Chemical Abstracts, vol. 112, No. 24, Jun. 11, 1990, Abstract No. 228202j, p. 771.

R. L. Tischer et al., "New Rare Earth Antiknock Additives That Are Potential Substitutes For Tetraethyl Lead", Chemical Abstracts, vol. 84, No. 12, Mar. 22, 1976, Abstract No. 76591y, p. 151.

M. I. Aizenberg et al., "Synthesis And Thermochromatographic Investigation Of Volatile Acetylacetonates of Americium And Lanthanoids", Chemical Abstracts, vol. 108, No. 20, May 16, 1988, Abstract No. 178960z, p. 790.

Drake et al, "Oxygen or Nitrogen Chelates stabilizing Barium and Yttrium β–Diketonates", Inorg. Chem. vol. 32, pp. 4464–4471 1993.

Poncelet et al, "Soluble and Volatile Yttrium and Copper Alkoxo–Acetylacetmato Derivatives, Synthesis and Crystal Structure of $Y_3(\mu_3,\eta^2-OC_2H_4OMe)_2(\mu_2,\eta^1-OC_2H_4OMe)(acac)_4$,", Inorg. Chem. vol. 29, pp. 2883–2885, 1990.

*Primary Examiner*—Shean C. Wu
*Attorney, Agent, or Firm*—Burns, Doane, Swecker & Mathis

[57] ABSTRACT

The invention provides rare earth compounds of formula $[(ML_3)_xA]_y$, where M is one or more of the rare earth metals and yttrium, L is a beta-diketone type ligand, A is a polyether or polyamine, and x and y are each 1 or 2. These compounds are precursors for chemical vapor deposition (CVD) of oxide layers in applications such as superconductors, piezoelectrics, microwaves, fuel cells, radiation detectors, optoelectronics, and catalysts. They are air and moisture stable, low melting, vacuum volatile at low temperatures leaving minimum residue and give good quality metal oxide deposits uncontaminated by fluorine. These compounds also have excellent solubility in a wide range of organic solvents, and are potentially useful as oil lubricant additives and in fuels.

14 Claims, 12 Drawing Sheets

RARE EARTH COMPOUNDS AND THEIR PREPARATION

This invention relates to rare earth compounds and their preparation. The term "rare earth" as used herein means a lanthanide element plus yttrium.

BACKGROUND

There is a considerable need for molecular precursors for Chemical Vapour Deposition (CVD) or Sol-gel processes to fabricate Lanthanide based materials. These are of potential importance as precursors of multimetallic oxides. For such precursors to find ready application, they should be stable in the gas phase and have good mass transport properties, thereby allowing the formation of a thin or thick film of either the metal or metal oxide to be deposited onto the desired substrate.

A major potential use of such precursors is in the synthesis of electroceramics, e.g. high temperature superconductor ceramic thin or thick films for use in electronic devices such as $YBa_2Cu_3O_{7-x}$; see P. P. Edwards et. al. Chemistry Britain, 1987, 23–26., $Pb_2Sr_2LnCu_3O_{8-x}$; M. O'Keefe and S. Hansen, J. Am. Chem. Soc. 1988, 110 1506, R. J. Cava et. al. Nature, (London), 1988, 336, 211–214; $La_{2-x}Sr_xCuO_4$; Bednorz and Muller, Z. Phys. B. Cond. Matter, 1986, 64, 189–195; piezoelectrics such as $LaCuO_2$; Müller-Buschbaum, Angew. Chem. 1989, 28, 1472–74 and phosphors and fuel cells.

Multimetallic oxide based ceramics are conventionally made by "heat and bake" technology; see D. Segal, Chemical Synthesis of Advanced Ceramic Materials, Cambridge University Press, Cambridge, 1991. This approach relies upon the intimate mixing of metal-oxygen based materials (e.g. metal carbonates, nitrates or hydroxides) by the use of techniques such as ball-milling, fusion processes, and uniaxial or hot isostatic pressing. Although these processes are attractive owing to their inherent simplicity and low cost, there are several inherent disadvantages. These are high temperature processing and post-annealing under a flow of oxygen gas, which ensures that any meta-stable phases cannot be accessed by this approach. There is also the added difficulty of phase inhomogenity, e.g. tetragonal and orthorhomic forms of $YCu_2Ba_3O_{7-x}$ present in the same material, and also the presence of ionic impurities (e.g. $BaCO_3$) frequently found at the grain boundaries.

An alternative strategy involves the use of metal alkoxides or β-diketonates; see Mehrotra et. al. Chem. Rev. 1991, 91, 1287–1302. These compounds are readily obtained as crystalline solids of known stoichiometry, high purity, good solubility in organic solvents, and long term stability in an inert atmosphere, and are sufficiently reactive that most reactions occur at or near room temperature. By using such materials fine control of molecular stoichiometry is possible and access to previously unobtainable metastable phases is achievable. These materials find extensive use in either sol-gel or chemical vapour deposition (CVD) processes, which involve the formation of either thick films (sol-gel spun coating) or ultrathin films (20 Å or less) for optical or microelectronic applications by CVD.

However, conventional lanthanide precursors for metal oxide films have several drawbacks, notably in the high residue left in commercial evaporators/bubblers for CVD and poor stability in the atmosphere. The use of fluorinated precursors results in the formation of $LnF_3$ which has to be removed with either superheated water vapour or air at elevated temperature to yield the required oxide based film. Therefore, to produce epitaxial or high quality films it is important to avoid the use of fluoride based compounds, even though such complexes have excellent vapour pressure and mass transport properties. Thus, as stated above, a precursor is required that vapourises without any decompostion and remains intact in the vapour phase for considerable time periods, i.e. for at least the length of time of the CVD process.

Lanthanide metal alkoxides and β-diketonates are well known materials; see K. S. Mazdiyasni et al Inorg. Chem., 1966, 3, 342–347; K. S. Mazdiyasni et al J. Less-Common Met., 1973, 30, 105–112, and R. C. Mehrotra et al, Metal Beta-diketones", Academic Press, London, 1978. A considerable degree of diversity has been previously found in their chemistry, notably with added Lewis bases; see T. Moeller et.al. Gmelin Handbook of Inorganic Chemistry, Sc, Y, La-Lu Rare Earth Elements Part D3, 8th Edn, Springer, Berlin, 1981. The most commonly used strategies for preparing volatile metal precursors are the use of bulky or alternatively fluorinated ligands that encapsulate the metal ions, and thus create discrete molecular species. This phenomenon occurs due to reduced intermolecular associations between metal centres, and therefore changes the orientation of the packing in the solid or liquid states; this in turn gives rise to enhanced thermal and mass transport properties. This approach has been recently adopted for the lanthanide complexes; see W. J. Evans et al., Inorg. Chem., 1989, 28, 4308–4314; M. J. McGeary et al., Inorg. Chem., 1991, 30, 1723–1724; E. H. Barash et al., Inorg. Chem., 1993, 32, 497–502; and R. E. Sievers, Science, 1978, 201, 217–223.

Because of their large ionic radii and coordination numbers the lanthanides are difficult to coordinatively saturate to yield monomeric complexes. Bulky ligands are limited in their ability to coordinatively saturate these highly Lewis acidic metals, i.e. poly-functionalised ligands have been extensively used, $[Y(OCH_2CH_2OMe)_3]_{10}$; see O. Poncolet et al. J. Chem. Soc., Chem. Commun., 1989, 1846–47; and $[Y_3(OCH_2CH_2OMe)_5(acac)_4$; see O. Poncolet et.al. Inorg. Chem., 1990, 29, 2885–2890. There are also other lanthanide complexes which contain simple ligands (e.g. $Pr^iO$ and $Bu^tO$), which are not sufficently electron rich to supply the electronic and steric requirements of these metals; see D. C. Bradley et al., Polyhedron, 1990, 9, 719–725 and 10, 1049–1056. This can lead to highly associated or indeed polymeric complexes, where the ligand is $MeO^-$ or $EtO^-$. To date, there has been little success at controlling the degree of oligomerisation of lanthanide molecular precursors.

There are a number of synthetic strategies which may be employed to prepare complexes. The most common route utilizes metathesis. A modification of this, especially where the $pK_a$ of the beta-diketone is too low (e.g. acac-H), is to use a water-ammonia mixture to drive the reaction to completion, e.g. see $[Ln(acac)_3(H_2O)]$, K. J. Eisentraut et al, J. Am. Chem. Soc., 1965, 87, 5254–5259; and G. S. Hammond et al, Inorg. Chem., 1963, 2, 73–75. See also T. Moeller et al. Gmelin Handbook of Inorganic Chemistry, Sc, Y, La-Lu Rare Earth Elements Part D3, 8th Edn, Springer, Berlin, 1981.

These known precursor syntheses show limited systematic control of aggregate size and give poorly characterised materials having poor moisture and thermal stability, and a short shelf life. It is therefore highly desirable to sythesise thermally stable and highly soluble materials which are suitable for either CVD or Sol-gel applications.

Compounds for this purpose must satisfy the following physical and chemical criteria:

defined identity and purity.

air and moisture stability for ease of handling.

low melting point for use in conventional CVD bubbler source chambers.

good solubility in a wide range of organic solvents.

significant volatility at low temperature.

clean pyrolysis at substrate temperatures.

give deposited layers free of unwanted impurities.

The present invention provides compounds meeting at least some of these criteria.

The compounds of the invention can be used as precursors for deposition of oxide layers by the chemical vapour deposition (CVD) technique. Rare earth oxides are employed alone or in conjunction with other metal oxides as ceramic or glass layers in a range of advanced materials such as superconductors, piezoelectrics, fuel cells, optoelectronics, radiation detectors, catalysts and to provide thermal and abrasion resistance. The compounds can be used in making devices for use in information technology, medical instrumentation and energy conservation.

The compounds of the invention are the rare earth compounds of formula:

$$[(ML_3)_xA]_y$$

where M represents one or more metals chosen from the rare earth metals and yttrium, L is a bidentate ligand, A is a polyether, polyamine or polyether-amine, and x and y are each 1 or 2 but are not both 2. They may be regarded as monomers of formula $ML_3A$ or bridged dimers of formula $(Ml_3)_2A$ or $(ML_3A)_2$.

The bidentate ligand L may be a β-diketonate anion containing a group of formula:

derived, more especially, from a compound of formula:

$$R^iR^{ii}R^{iii}CCOCHR^{iv}COR^v$$

where $R^i$, $R^{ii}$, $R^{iii}$, $R^{iv}$ and $R^v$ are each hydrogen, alkyl of 1 to 6 carbon atoms optionally substituted by fluorine or phenyl, or fluorine, and $R^v$ may also be alkyloxy of 1 to 6 carbon atoms optionally substituted by fluorine, amino, alkylamino, or dialkylamino in which each alkyl has 1 to 6 carbon atoms optionally substituted by fluorine.

Preferably the ligand L is derived from a β-diketone, especially from one or more of acetylacetone, tetramethylheptanedione, trifluoroacetylacetone, hexafluoroacetylacetone, and 1,5-diphenylpentanedione.

The polyether, polyamine or polyether-amine A may be represented by the formula:

$$R^i—Y(CR^{ii}R^{iii}CR^{iv}R^v—Y)_nR^{vi}$$

where each of $R^i$, $R^{ii}$, $R^{iii}$, $R^{iv}$, $R^v$ and $R^{vi}$ is hydrogen or alkyl of 1 to 6 carbon atoms, Y is —O—, —NR$^{vii}$ (where R$^{vii}$ is hydrogen or alkyl of 1 to 6 carbon atoms), or a mixture thereof, and n is 1 to 10.

Preferred polyethers may be represented by the formula:

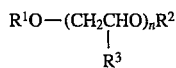

wherein $R^1$, $R^2$ and $R^3$ are each hydrogen or alkyl of 1 to 4 carbon atoms and n is 1 to 10, and preferred polyamines by the formula:

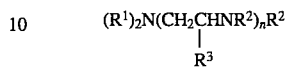

wherein $R^1$, $R^2$ and $R^3$ and n are as hereinbefore defined

Especially preferred polyethers are those wherein $R^1$ and $R^2$ are each alkyl of 1 to 4 carbon atoms, $R^3$ is hydrogen, and n is an integer from 1 to 7, more particularly monoglyme, diglyme, triglyme, tetraglyme, and/or heptaglyme.

Especially preferred polyamines are those wherein $R^1$ and $R^2$ are each alkyl of 1 to 4 carbon atoms, $R^3$ is hydrogen, and n is an integer from 1 to 3, more particularly tmeda, pmdeta, and/or hmteta.

When A is derived from monoglyme, tetraglyme, tmeda, or pmedta, the monomeric structure is generally formed, i.e. $ML_3A$. When A is triglyme or heptaglyme a bridged dimeric compound is usually obtained, i.e. $(ML_3)_2A$, and with diglyme, a dimeric structure having two bridging diglyme molecules can be obtained, i.e. $(ML_3A)_2$.

Type I structure x=1, y=1

An example of this type of monomeric structure is shown by [La(thd)$_3$(tetraglyme)]. The lanthanum atom binds to all three bidentate thd beta-diketone ligands and to only three of the five possible oxygen atoms of the tetraglyme ligand. Thus the lanthanum atom prefers to adopt a nine-coordinate rather than a possible eleven-coordinate site. A square antiprismatic geometry is observed for this complex, with the ninth coordinating oxygen atom [O(5)] capping one of the square faces. In this complex the coordinated portion of the glyme has one short La-O bond, 2.706(7) Å [O(2)], and two long La-O bonds, 2.781(6) [O(5)] and 2.751(7) Å [O(8)]. The most noticeable and clearly unusual feature of this complex is the presence of the uncoordinated portion of the tetraglyme chain C(9)–C(15) which, with the exception of the terminal methoxy bond, is approximately planar. A study of a space-filling model of this complex indicates that the coordination of an additional glyme oxygen centre is not favourable because of the presence of the three tightly held thd beta-diketone ligands and with three of the five available glyme oxygen atoms saturating the lanathanum metal centre.

Type II structure x=2, y=1

An example of this type of structure is shown by [{Eu(thd)$_3$}$_2$(triglyme)] which consists of two Eu(thd)$_3$ moieties linked together by a triglyme ligand involving a unique bonding orientation. Both metal atoms are eight coordinate with the overall coordination polyhedron being distorted square antiprismatic. One of the most interesting features of this complex is the observation that the triglyme can act as both a chelate and also as a bridging ligand via the central ethylene bridge [C(37)–C(38)]. This structure allows the utilisation of all four potential binding sites of the glyme ligand.

The coordination numbers of the metals in these complexes are eight or nine which is believed to be the principal reason for the advantageous chemical and physical properties of the compounds (see Table 1 below). Thermal behaviour has been studied by thermogravimetric analysis and clearly reveals that these materials volatilize into the gaseous phase intact, and the first derivative peak shows essentially 96±2% sublimation for these compounds. The related melting behaviour has been examined by the use of differential scanning calorimetry which has demonstrated a marked reduction in melting point from 200°–250° C. to 60°–130° C. on the addition of the multidentate Lewis base ligand.

The compounds of the invention have an advantageously low molecular weight in relation to the amount of rare earth metal or yttrium present. Thus the average molecular weight per metal atom is usual below 2000 and preferably below 1500, and in especially advantageous cases can be below 1000.

The following Table gives examplary physical properties of some compounds of the invention.

TABLE 1

| Compound | m.p./°C. | evaporation temp. °C./ $10^{-2}$ mm Hg. | $T_{50\%}$/ °C. | residue % | pyrolysis temp. °C. |
|---|---|---|---|---|---|
| [La(thd)$_3$(tetraglyme)][a] | 59.9 | 110 | 287 | 3.2 | 312 |
| [Eu(thd)$_3$]$_2$(triglyme) | 128.2 | 115 | 258 | 3.7 | 287 |
| [Tb(thd)$_3$]$_2$(triglyme) | 115.5 | 120 | 242 | 4.5 | 330 |
| [Y(thd)$_3$]$_2$(triglyme) | 95.4 | 100 | 223 | 2.6 | 255 |
| [Pr(thd)$_3$(triglyme)] | 122 | 140 | 248 | 2.3 | 385 |
| [EuY(thd)$_6$](triglyme) | 113.8 | 105 | 246 | 5.1 | 272 |
| [Tb(thd)$_3$(diglyme)]$_2$ | 64.3 | 110 | 257 | 2.2 | 288 |
| [Y(thd)$_3$]$_2$(hmteta) | 123.1 | 120 | 251 | 1.9 | 282 |
| [LaTm(thd)$_6$](triglyme) | 55.9 | 115 | 246 | 4.9 | 286 | a. This complex is the only material observed to lose its polydentate ligand in the vapour phase to yield [La$_2$(thd)$_6$] at ca. 180° C.

The compounds of the invention have excellent solubility in a wide range of organic solvents, e.g. aliphatic solvents, such as n-pentane, hexane, and heptane; aromatic solvents such as benzene, toluene and xylene and coordinating solvents, e.g. diethylether, tetrahydrofuran, di-n-butylether, dimethylsulphoxide, acetonitrile, pyridine, and chloroform. Indeed, the outstanding solubility shown by the majority of the new compounds ensures that they do not crystallise out of organic solvents. If desired in a crystalline form, then all the organic solvent must be removed, and the compound is crystallised from the oily material remaining.

The excellent solubility of the new compounds in organic solvents makes them suitable for use as additives in lubricants and fuels, including fuels for internal combustion engines and, more especially, hydrocarbon fuels for compression ignition (diesel) engines.

The compounds stated in the prior art to have formulae such as "Ln(thd)$_3$" where Ln is any rare earth metal or yttrium, actually contain coordinated water or other adducted ligands. Unadducted molecules are oligomers with melting points in the range 200°–260° C. with evaporation commencing at a slightly higher temperature. Our X-ray studies have shown that these compounds are dimeric complexes, e.g. [Gd$_2$(thd)$_6$], with two bridging thd ligands. Unless strictly anhydrous conditions are maintained during preparation they are heavily contaminated with hydrated species which behave unpredictably because of intramolecular hydrolysis when the compounds are heated to their vacuum evaporation points. In general the rate of evaporation of the prior art compounds declines with time and source chambers become clogged with residue.

These complexes have infrared absorption bands at 1609±5, 1586±5 and 1540±5 cm$^{-1}$, assigned to $v(C\text{---}O)$ stretching modes and bands at 1575±2 and 1500±5 cm$^{-1}$ assigned to the $v(C\text{---}C)$ stretching modes. In the compounds of the invention the glyme ligand $v(C\text{---}O)$ bands were observed in the region 1130±10 cm$^{-1}$, a shift of ca. 50 cm$^{-1}$ compared with the prior art compounds containing no glyme ligand, indicative of strong M—O bonding.

A reason for the oligomerisation and hydration of the prior art compounds is the lack of controlled saturation of the coordination sphere of the metal ion. The compounds of the invention have linear polyether molecules whose oxygen atoms act as Lewis base donors to saturate the Lanthanide metal ion coordination sphere. The outermost architecture of the adducted molecule comprises hydrocarbon groups whose neighbour interactions are weak Van der Waals attractions. Consequently the molecules of this invention exhibit little tendency to associate, and have melting and evaporation points 80°–150° C. below those of the prior art compounds. Moreover, they do not pick up water upon air exposure.

Additionally, the thermal stability of the compounds of the invention in the vapour phase assists deposition by providing an activated species prior to the final step of pyrolysis to the metal oxide. This is another advantage of the compounds of the invention, see FIGS. 9–15. The majority of the complexes studied exhibit a sharp reversible melting point in their DSC spectra. The TGA curve shapes for these compounds reveal the presence of a single isothermal step, and near complete vapourisation of these materials by ca. 300° C.

The absence of water in the compounds of the invention is of especial importance. Anhydrous synthesis route I below employs either metal amide or alkoxide starting materials dissolved in hydrocarbon solvent and gives excellent yields. However, these materials are expensive, and routes II or III below give almost as good yields starting from cheaper hydrated salts dissolved, e.g., in methanol. The presence of a small excess of the polyether or amine is apparently sufficient to expel adducted water from the metal coordination sphere.

According to a feature of the invention, the new compounds are made by reacting a rare earth compound of formula:

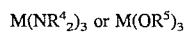

M(NR$^4$$_2$)$_3$ or M(OR$^5$)$_3$ where M represents one or more metals chosen from the rare earth metals and yttrium, R$^4$ is alkyl of 1 to 4 carbon atoms or trimethylsilyl, and R$^5$ is alkyl of 1 to 4 carbon atoms optionally substituted by alkoxy of 1 to 4 carbon atoms with a bidentate ligand LH and a polyether, polyamine or polyether amine. The reaction may, more particularly, be carried out in a hydrocarbon solvent.

The reaction may be represented:

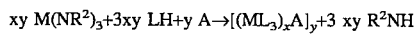

Where R=Et, Pr$^i$ or SiMe$_3$ are the preferred ligands, or

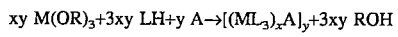

Where R=Pr$^i$ or Bu$^t$ are the preferred ligands, but may also be, e.g. Me, Et, Pr$^n$, or MeOCH$_2$CH$_2$—.

According to another feature of the invention, the new compounds are made by reacting a rare earth compound of formula: MZ$_3$(H$_2$O)$_6$ where M represents one or more metals chosen from the rare earth metals and yttrium and Z represents an anion with an alkali metal derivative of the bidentate ligand LH and a polyether, polyamine, or polyetheramine A. The reaction may be carried out in an alcohol solvent using a halide, carboxylate, sulphate or nitrate of the rare earth metal.

The reaction may be represented:

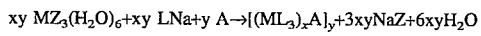

where M, L, A, x and y are as defined above and Z=halide, carboxylate, nitrate, or sulphate.

According to yet another feature of the invention, the new compounds are made by reacting a rare earth oxide, hydroxide or carbonate with the bidentate ligand LH and a polyether, polyamine or polyether-amine A. The reaction may be carried out in an organic, e.g. hydrocarbon, or aqueous solvent. It may be represented:

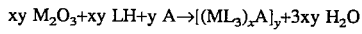

where M, L, A, x and y are as defined above.

In the compounds of the invention the metal centres are coordinatively saturated with the combined use of both a chelating type of Lewis base ligand, i.e. a glyme or amine, and a chelating bidentate group, e.g. a diketone. This presumably gives rise to the exceptional stability in the atmosphere of the new compounds, since the chelating ligands are less readily hydrolysed than monodentate ligands. Secondly, the use of multidentate ligands reduces the possibility of interactions between monomeric units. Third, the use of a preformed metal beta-diketonate (whether anhydrous or as a hydrate) leads to water free products. Thus anhydrous metal diketone derivatives can be prepared by a low cost route, e.g. by the use of simple hydrated complexes prepared via metathesis in alcohol/aqueous media. The observation that water can be removed from the hydrated starting materials is important, and only one equivalent of glyme ligand is needed and not an excess.

The compounds show a further novel property in several cases, e.g. [La(thd)$_3$(tetraglyme)] (see FIG. 1), [Gd(thd)$_3$]$_2$(tetraglyme) (see FIG. 7), [Y(thd)$_3$]$_2$(hmteta) (see FIG. 3), and [Gd(thd)$_3$]$_2$(heptaglyme) (see FIG. 6). In these complexes a portion of the multidentate ether or amine chain is not coordinated to the lanthanide metal centre and may be used to react with an incoming metal complex (e.g. a transition metal or lanthanide) to synthesise previously inaccessible metal combinations, e.g. La—Cu, La—Cu$_2$, La—Mn, Y—Zr, or Gd—Ce.

The following abbreviations are used herein:

| | | |
|---|---|---|
| thd | tetramethylheptanedionate | Me$_3$CCOCHCOCMe$_3$ |
| acac | acetylacetonate | MeCOCHCOMe |
| tfa | trifluoroacetylacetonate | F$_3$CCOCHCOMe |
| hfa | hexafluoroacetylacetonate | F$_3$CCOCHCOCF$_3$ |
| dpp | 1,5-diphenylpentanedionate | PhCH$_2$COCHCOCH$_2$Ph |
| monoglyme (or dme) | monoethyleneglycol dimethyl ether | Me(OCH$_2$CH$_2$)OMe |
| diglyme | diethyleneglycol dimethyl ether | Me(OCH$_2$CH$_2$)$_2$OMe |
| triglyme | triethyleneglycol dimethyl ether | Me(OCH$_2$CH$_2$)$_3$OMe |
| tetraglyme | tetraethyleneglycoldimethyl ether | Me(OCH$_2$CH$_2$)$_4$OMe |
| heptaglyme | heptaethyleneglycol dimethyl ether | Me(OCH$_2$CH$_2$)$_7$OMe |
| tmeda | tetramethylethylenediamine | Me$_2$NCH$_2$CH$_2$NMe$_2$ |
| pmdeta | pentamethyldiethylenetriamine | Me$_2$NCH$_2$CH$_2$N(Me)CH$_2$CH$_2$NMe$_2$ |
| hmteta | hexamethyltriethylenetetramine | Me$_2$NCH$_2$CH$_2$\{N(Me)CH$_2$CH$_2$\}$_2$NMe$_2$ |

BRIEF DESCRIPTION OF THE DRAWINGS

In the accompanying drawings.

FIG. 1 [La(thd)$_3$(tetraglyme)]—example of type I compound, see Example 10.

FIG. 2 [Y(thd)$_3$]$_2$(triglyme)—example of type II compound, see Example 2.

FIG. 3 [Y(thd)$_3$]$_2$(hmteta)—example of type II compound with polyamine adduct, see Example 5.

FIG. 4 [EuY(thd)$_6$(triglyme)]—example of type II compound with different metal atoms in a single structure, see Example 7.

FIG. 5 [Pr(thd)$_3$(triglyme)][Pr(thd)$_3$]$_2$(triglyme)—example of compound adopting type I and type II structure simultaneously, see Example 17.

FIG. 6 [Gd(thd)$_3$]$_2$(heptaglyme)—example of type II compound with added presence of two available glyme oxygen atoms, see Example 34.

FIG. 7 [\{Gd(thd)$_3$\}$_2$(tetraglyme)]—example of a type II compound, see Example 33.

FIG. 9 [La(thd)$_3$(tetraglyme)] (a) heat flow (b) weight loss, product of Example 10.

FIG. 10 [Eu(thd)$_3$]$_2$(triglyme) (a) heat flow (b) weight loss, product of Example 28.

FIG. 11 [Tb(thd)$_3$]$_2$(triglyme) (a) heat flow (b) weight loss, product of Example 38.

FIG. 12 [EuY(thd)$_6$(triglyme)] (a) heat flow (b) weight loss, product of Example 7.

FIG. 13 [Pr(thd)₃(triglyme)][Pr(thd)₃]₂(triglyme) (a) heat flow (b) weight loss, product of Example 17.

FIG. 14 [LaTm(thd)₆(triglyme)] (a) heat flow (b) weight loss, product of Example 13.

FIG. 15 [Y(thd)₃]₂(hmteta) (a) heat flow (b) weight loss, product of Example 5.

Figure 1:
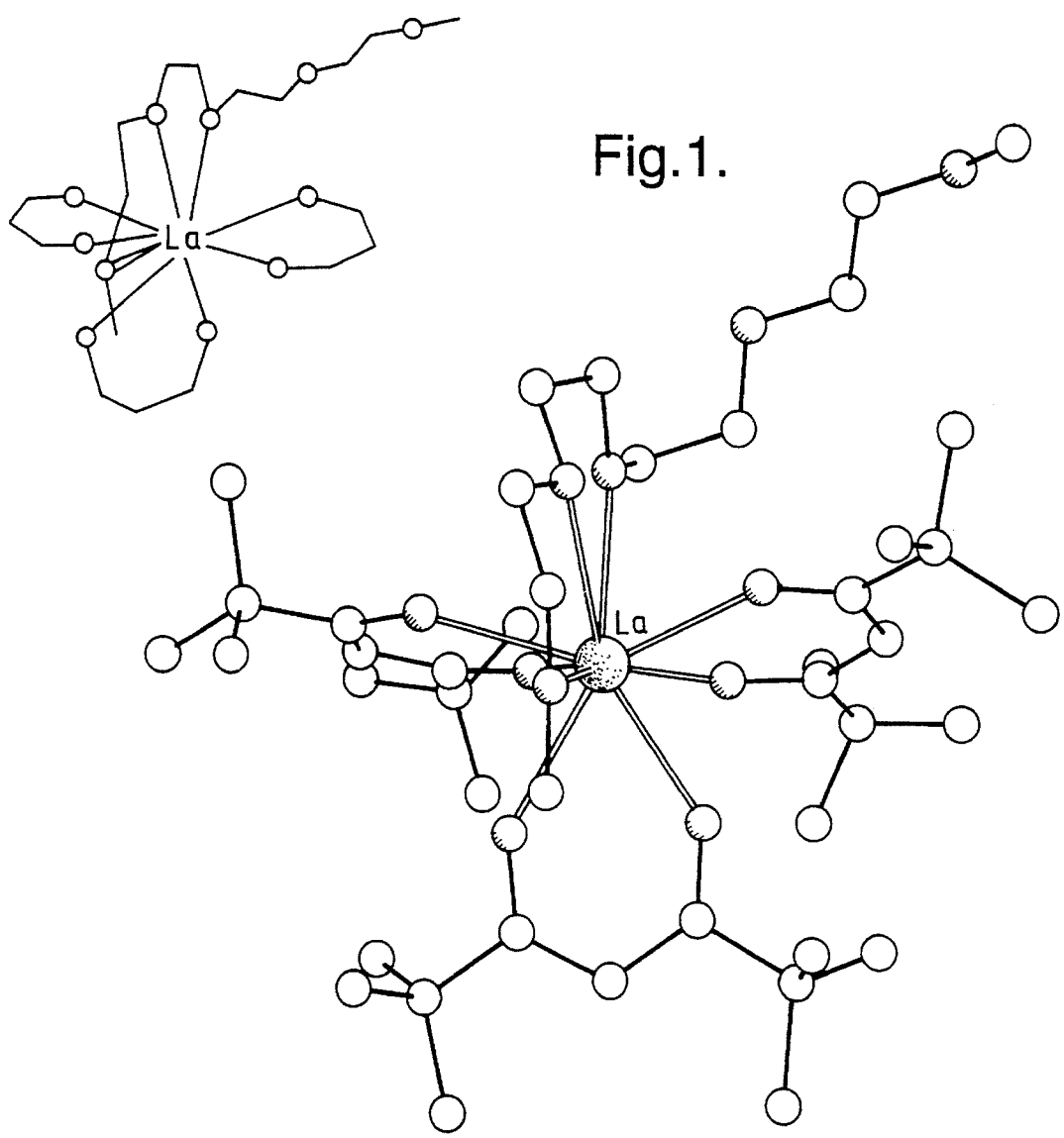
FIGS. 1–7 are molecular structures determined by X-ray crystallography of selected compounds described in the Examples.

The following Examples illustrate the invention. The x-ray crystal structures were generated with SHELX 91 using a local modification, DIFABS 2, operating on a PC. In the drawings (FIGS. 1–8), as is conventional, for clarity tert-butyl groups are not shown. The differential scanning and thermogravimetric analyses (FIGS. 9–15) were determined on Polymer Laboratories PL 1500 simultaneous Thermal Analysis equipment.

EXAMPLES

1. YTTRIUM TRIS-THD DIGLYME [Y(thd)₃(diglyme)]₂—an example of a type III compound.

Sodium hydroxide (12 g, 300 mmole) is dissolved in 75 ml methanol and stirred into a solution of thdH (55.2 g, 300 mmole) in 75 ml methanol. Then yttrium chloride hexahydrate (30.4 g, 100 mmole) is dissolved in 100 ml warm methanol and added portionwise with stirring to the thdNa solution. After completing the addition the solution is stirred for 10 minutes and then poured with vigorous stirring into 1 liter of water. The precipitated product is immediately filtered off, washed on the filter with water, turned into 100 ml hexane and warmed to dissolve. The organic solution is separated from residual water and insolubles, stripped until solid begins to appear then set aside to crystallise. The product is filtered and vacuum dried as [Y(thd)₃(H₂O)]ₙ.

The [Y(thd)₃(H₂O)]ₙ (57.5 g, 90 mmole) is dissolved with warming in 250 ml of hexane, diglyme (12 g, 90 mmole) is added and the solution stirred at room temperature for 1 hour. It is then stripped to an oil and set aside at 20° C. to crystallise.

Yield is 61 g, 85% of colourless air stable crystals.

Melting point 86°–89° C.

Microanalysis Found: C, 60.8; H, 9.2. Calcd. YC₃₉H₆₉O₉, C, 61.1; H, 9.1%.

¹H NMR in C₆D₆ at 270 MHz: δ1.19 (s, CH₃), δ3.22 (s, OCH₃), δ3.41 (s, OCH₂-b), δ3.57 (s, OCH₂-a), δ5.82 (s, CH). Integral of thd:diglyme is 3:1.

Freezing point depression in benzene yields a molecular weight of 1490±70 (calc. 1544).

2. YTTRIUM TRIS-THD TRIGLYME [(Y(thd)₃)₂(triglyme)]—an example of a type II compound.

Yttrium isopropoxide (85 g, 32 mmole) is dissolved in 250 ml of cyclohexane and then thdH (176 g, 96 mmole) added and the solution refluxed for 2 hours. A short column is then fitted to the flask and the cyclo-hexane/isopropylalcohol azeotrope boiling at 68° C. is removed. On cooling the product crystallises out and is then filtered and vacuum dried as [Y(thd)₃]₂.

The [Y(thd)₃]₂ (64.8 g, 100 mmole) is dissolved with warming in 200 ml of hexane, triglyme (8.6 g, 50 mmole) is added and the solution stirred at room temperature for 1 hour. It is then stripped to an oil and set aside at 20° C. to crystallise.

Yield is 65 g, 89% of colourless air stable crystals.

Melting point 77°–81° C.

Microanalysis Found: C, 60.8; H, 9.2. Calcd. Y₂C₇₄H₁₃₂O₁₆, C, 61.1; H, 9.1%.

Infrared spectrometry (Nujol ν cm⁻¹): 1576(s), 1537(s), 1504 (s), 1490(s), 1422(s), 1302(m), 1250(m), 1223(s), 1180(s), 1137(s), 406(w).

¹H NMR in C₆D₆ at 270 MHz: δ1.20 (s, CH₃), δ3.26 (s, CH₃), δ3.33 (s, OCH₂-c), δ3.60 (s, OCH₂-b), δ3.74 (s, OCH₂-a), δ5.85 (s, CH). Integral of thd:triglyme is 6:1.

Freezing point depression in benzene yields a molecular weight of 1240±75 (calc. 1276).

Figure 2:
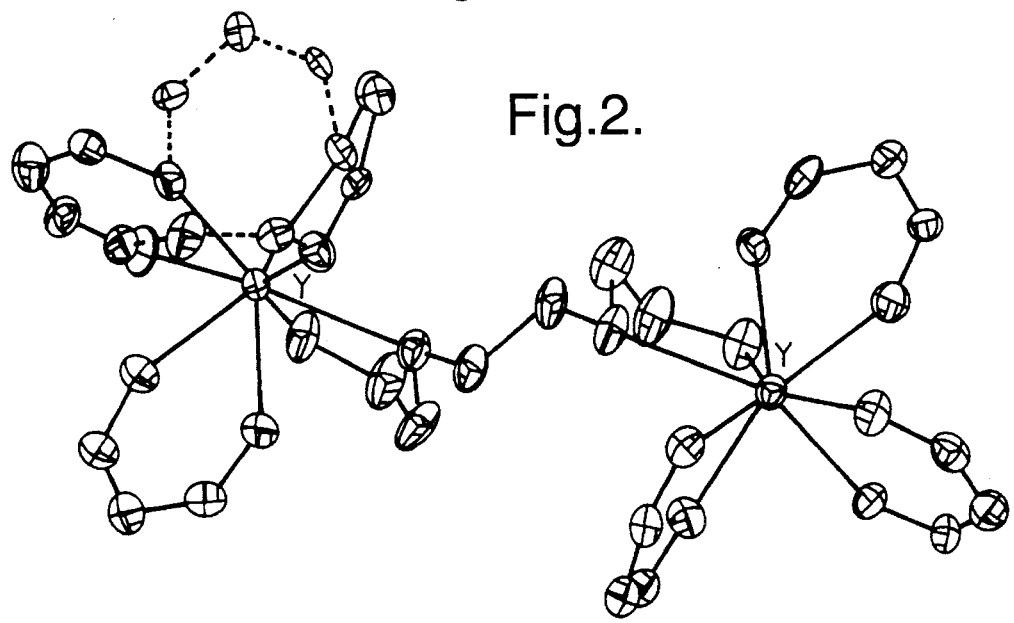

X-ray crystal structure—FIG. 2.

3. YTTRIUM TRIS-HFA TRIGLYME [(Y(hfa)₃)₂(triglyme)]— an example of a type II compound.

Yttrium hexamethyldisilazide (100 g, 17.5 mmole) is dissolved in 400 ml of hexane and then hfaH (109 g, 52.5 mmole) added and the solution refluxed for 2.5 hours. The solvent and liberated hmdzH were removed under vacuum and the off-white solid recrystallised from chloroform-hexane. Yield of [Y(hfa)₃]₂ is 102 g, 83%.

The [Y(hfa)₃]₂ (50 g, 7.04 mmole) is dissolved with warming in 200 ml of hexane, triglyme (12.3 g, 7.04 mmole) is added and the solution stirred at room temperature for 1 hour. It is then stripped to an oil and set aside at 20° C. to crystallise.

Yield is 48 g, 77% of colourless air stable crystals.

Melting point 60°–62° C.

Microanalysis Found: C, 27.5; H, 1.5. Calcd. Y₂C₃₆H₂₀F₃₆O₁₅, C, 27.8; H, 1.3%.

Infrared spectrometry (Nujol ν cm⁻¹): 1572(s), 1533(m), 1500 (s), 1493(s), 1426(m), 1306(s), 1252(m), 1219(s), 1184(s), 1137(s),404(w).

¹H NMR in C₆D₆ at 270 MHz: δ3.24 (s, OCH₃), δ3.30 (s, OCH₂-c), δ3.57 (s, OCH₂-b), δ3.72 (s, OCH₂-a), δ5.92 (s, CH). Integral of hfa:triglyme is 6:1.

Freezing point depression in benzene yields a molecular weight of 1530±70 (calc. 1554).

4. YTTRIUM TRIS-TFA TETRAGLYME [(Y(tfa)₃)₂(tetraglyme)]—an example of a type II compound.

The Y₂O₃ as a finely ground powder (20 g, 88.5 mole) is suspended in 75 ml of toluene, containing tfaH (60 ml, 392 mmole) tetraglyme (39.2 ml, 177 mmole) is added and the solution refluxed until >90% of the metal oxide has dissolved. It is then filtered and stripped to an oil and set aside at 20° C. to crystallise.

Yield is 41.5 g, 61% of colourless air stable crystals.

Melting point 74°–76° C.

Microanalysis Found: C, 36.7; H, 3.8. Calcd. Y₂C₄₀H₄₆F₁₈O₁₇, C, 36.4; H, 3.5%.

¹H NMR in C₆D₆ at 270 MHz: δ1.26 (s, CH₃), δ3.11 (s, OCH₃), δ3.22 (s, OCH₂-d), δ3.38 (s, OCH₂-c), δ3.40 (s, OCH₂-b), δ3.44 (s, OCH₂-a), δ5.91 (s, CH). Integral of tfa:tetraglyme is 6:1.

Freezing point depression in benzene yields a molecular weight of 1460±80 (calc. 1498).

5. YTTRIUM TRIS-THD HEXAMETHYLTRIETHYLENETETRAMINE [(Y(thd)₃)₂(HMTETA)]—an example of a type II compound.

The first part of the preparation employs a similar method to example 1, to yield [Y(thd)₃(H₂O)]ₙ.

The [Y(thd)₃(H₂O)]ₙ (0.72 g, 1.09 mmole) is dissolved with warming in 10 ml of hexane, hmteta (0.29 ml, 1.09 mmole) is added and the solution stirred at room temperature for 1 hour. It is then stripped to an oil and set aside at 20° C. to crystallise.

Yield is 0.76 g, 92% of colourless air stable crystals.

Melting point 109°–112° C.

Microanalysis Found: C, 61.9; H, 9.5. Calcd. $Y_2C_{78}H_{144}O_{12}N_4$, C, 62.2; H, 9.6%.

$^1$H NMR in $C_6D_6$ at 270 MHz: δ1.20 (s, $CH_3$), δ2.21 (s, NMe), δ2.34 (s, $NMe_2$), δ2.59 (d, $NCH_2$), δ5.86 (s, CH). Integral of thd:hmteta is 6:1.

Sublimation: The complex sublimes intact in essentially quantitative yield in the range 90°–110° C. at 5×10$^{-3}$ torr.

Freezing point depression in benzene yields a molecular weight of 1475±50 (calc. 1506).

Figure 3:
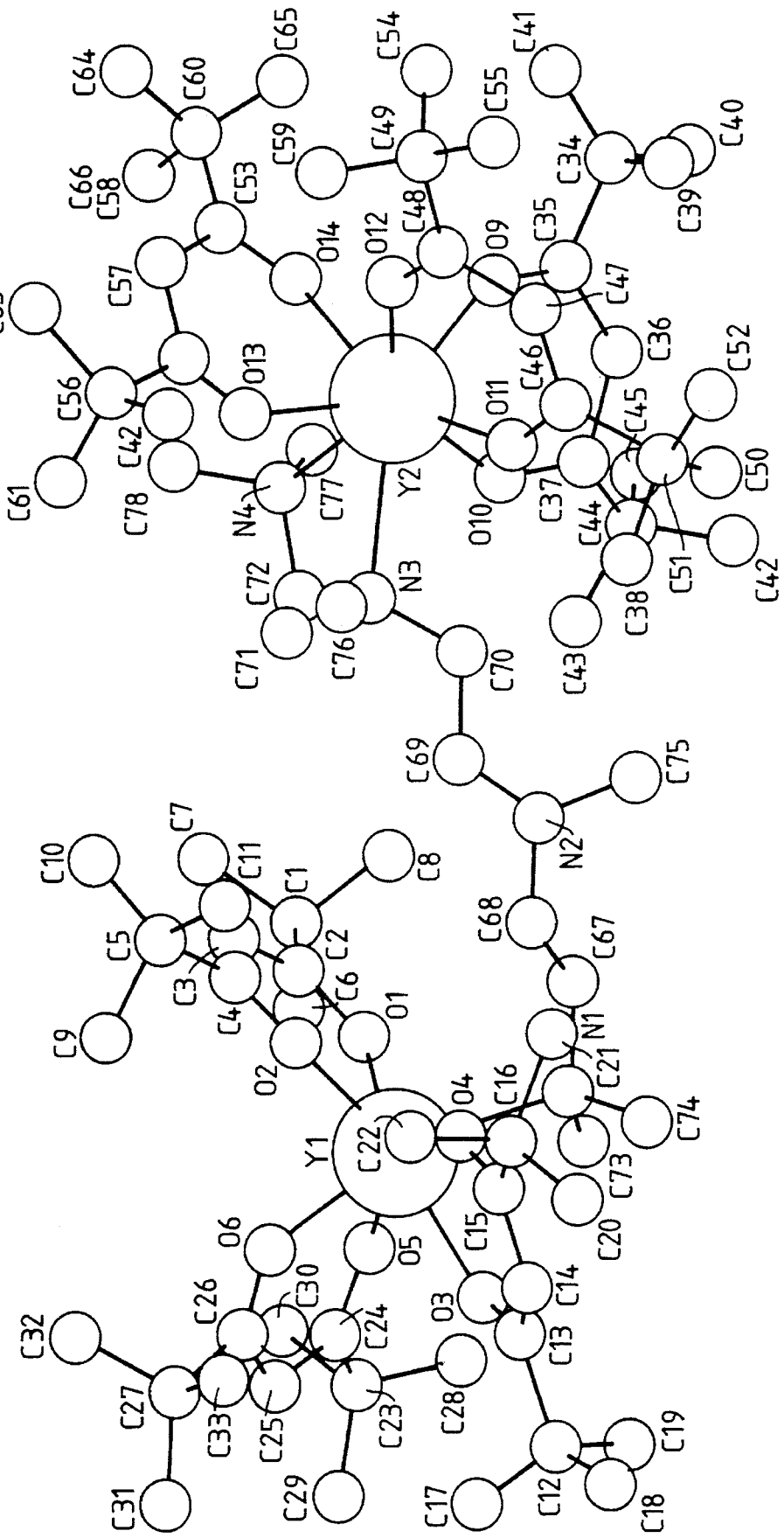

X-ray crystal structure—FIG. 3.

6. YTTRIUM TRIS-Ph$_2$ACAC TETRAMETHYLETHYLENEDIAMINE
[Y(Ph$_2$acac)$_3$(TMEDA)]—an example of a type I compound.

The first part of the preparation employs a similar method to example 3, to yield [Y(Ph$_2$acac)$_3$]$_n$.

The [Y(Ph$_2$acac)$_3$]$_n$ (4.0 g, 5.28 mmole) is suspended in 50 ml of chloroform, tmeda (0.62 ml, 5.28 mmole) is added and the solution stirred at room temperature for 1 hour. It is then stripped to an oil and set aside at 20° C. to crystallise.

Yield is 4.25 g, 92% of colourless air stable crystals.

Melting point 160°–163° C.

Microanalysis Found: C, 70.2; H, 5.9. Calcd. $YC_{51}H_{49}O_6N_2$, C, 70.0; H, 5.6%.

$^1$H NMR in $CDCl_3$ at 270 MHz: δ2.08 (s, NMe), δ2.27 (s, $NMe_2$), δ5.86 (s, CH), δ7.06 (m, Ph), δ7.18 (m, Ph), δ7.34 (m, Ph). Integral of Ph$_2$acac:tmeda is 3:1.

Mass Spectrometry (EI$^+$): 874 [Y(Ph$_2$acac)$_3$(tmeda)]$^+$ (7%), 754 [Y((Ph$_2$acac)$_3$]$^+$ (34%) and lower mass species.

7. YTTRIUM-EUROPIUM TRIS-THD TRIGLYME
[YEu(thd)$_6$(triglyme)]—an example of a type II compound with two different metals.

The first part of the preparation employs a similar method to example 1, the quantities being sodium hydroxide (12 g, 300 mmole), thdH (55.2 g, 300 mmole), europium chloride hexahydrate (23.7 g, 50 mmole) and yttrium chloride hexahydrate (15.2 g, 50 mmole) to yield [Y(thd)$_3$(H$_2$O)]$_n$ and [Eu(thd)$_3$(H$_2$O)]$_n$.

The [Y(thd)$_3$(H$_2$O)]$_n$ (28.8 g, 45 mmole) and [Eu(thd)$_3$(H$_2$O)] (31.5 g, 45 mmole) are dissolved on with warming in 250 ml of hexane, triglyme (8 g, 45 mmole) is added and the solution stirred at room temperature for 1 hour. It is then set stripped to an oil and set aside at 20° C. to crystallise.

Yield is 62 g, 87% of colourless air stable crystals.

Melting point 95°–97° C.

Microanalysis Found: C,56.4; H, 8.2. Calcd. $YEuC_{74}H_{132}O_{16}$, C, 56.1; H, 8.1%.

$^1$H NMR in $C_6D_6$ at 270 MHz: δ–0.52 (s, $CH_3$), δ0.4 (s, br, $OCH_3$), δ1.26 (s, $CH_3$), δ8.0 (s, $OCH_2$-c+b), δ9.47 (s, $OCH_2$-a), δ5.99 (s, CH). Integral of thd:triglyme is 6:1.

Freezing point depression in benzene yields a molecular weight of 1470±75 (calc. 1519).

Figure 12A:
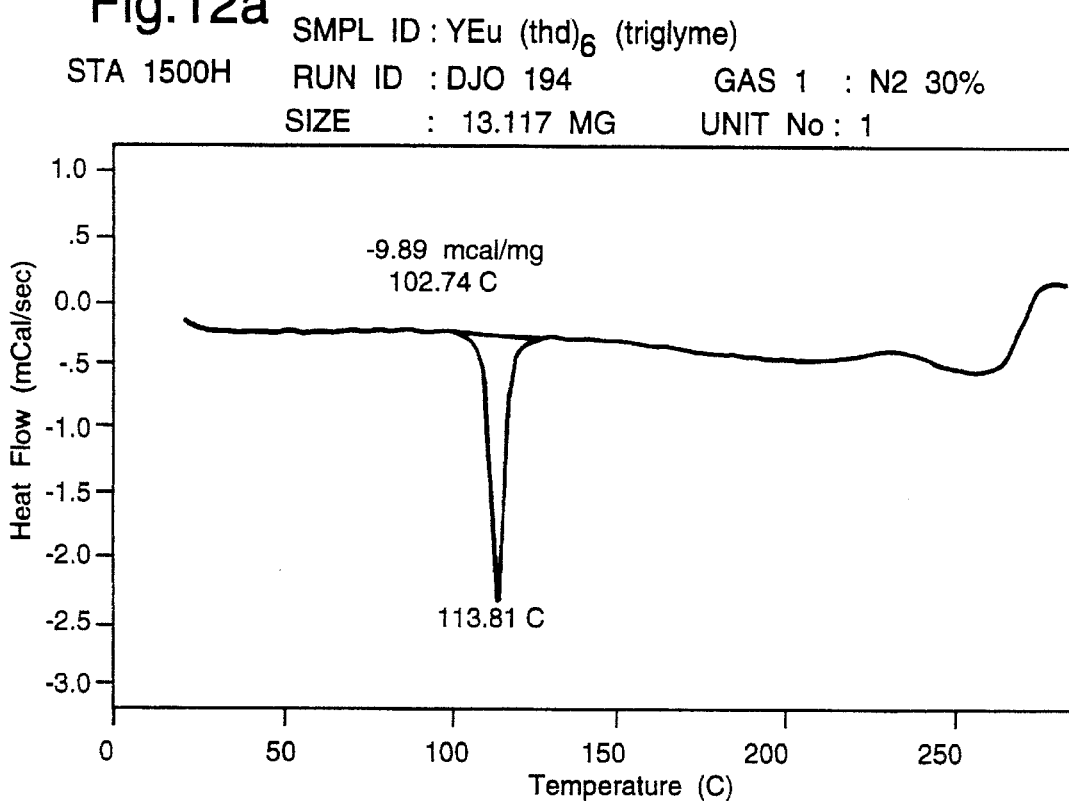
Figure 12B:
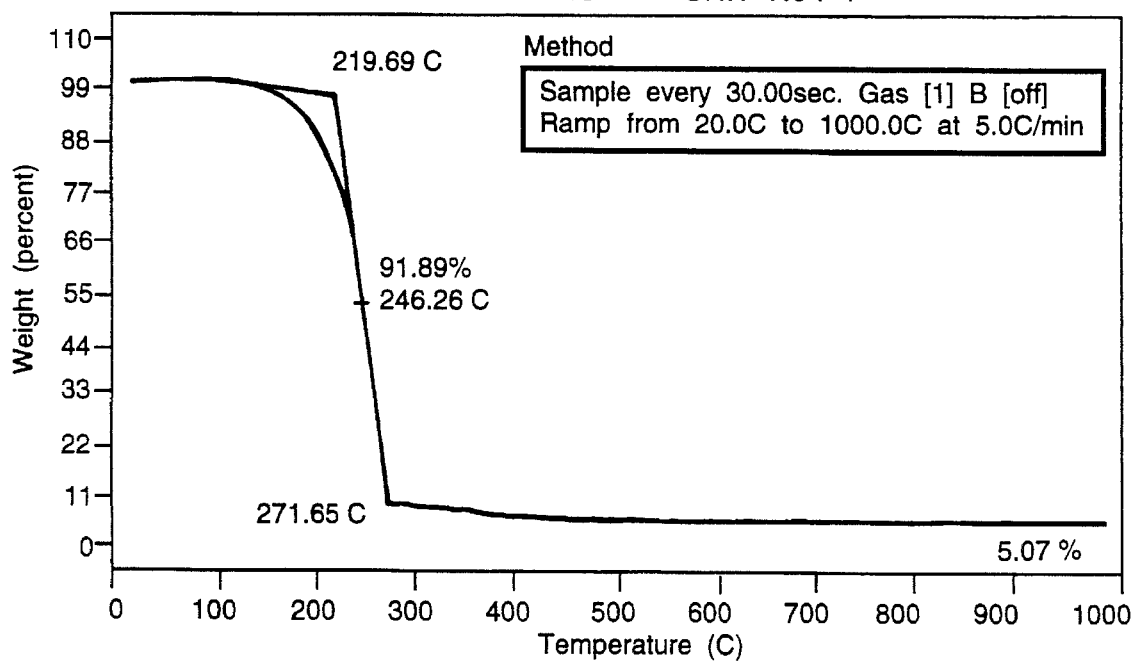

Differential scanning analysis and thermogravimetric analysis see FIGS. 12a and 12b.

Figure 4:
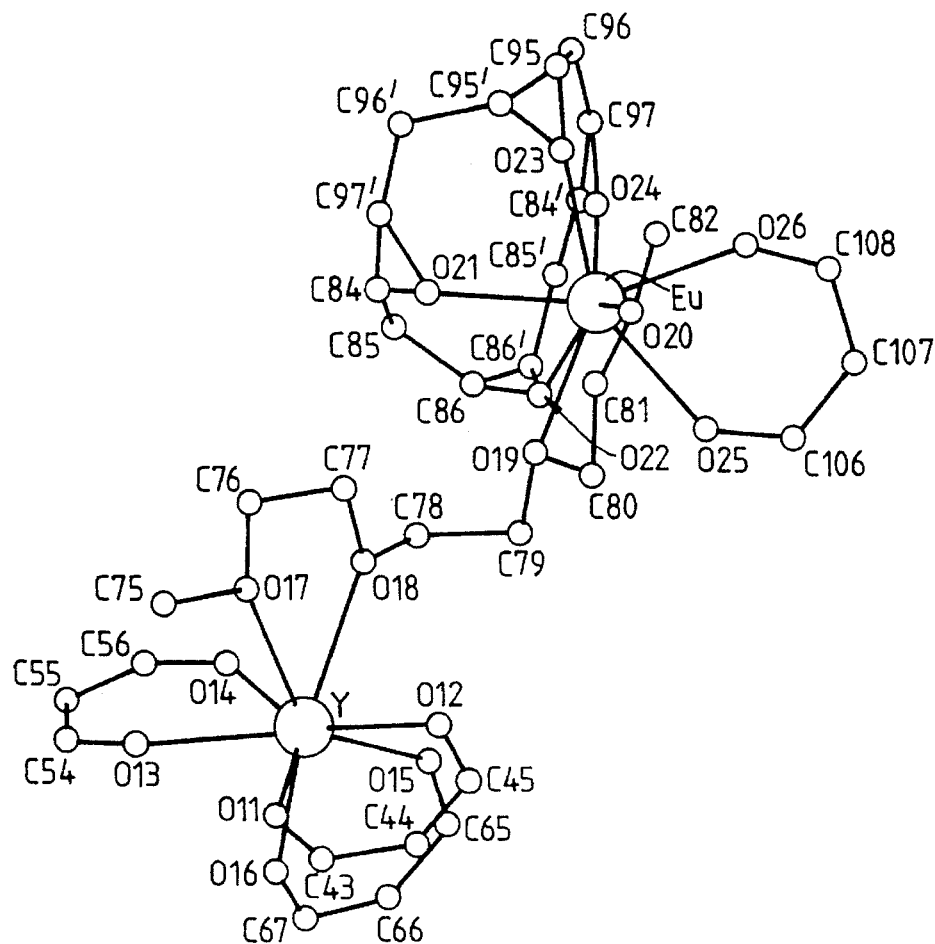

X-ray crystal structure—FIG. 4.

8. YTTRIUM-TERBIUM TRIS-THD TRIGLYME
[YTb(thd)$_6$(triglyme)]—an example of a type II compound with two different metals.

The first part of the preparation employs a similar method to example 1, the quantities being sodium hydroxide (12 g, 300 mmole), thdH (55.2 g, 300 mmole), terbium chloride hexahydrate (24.0 g, 50 mmole) and yttrium chloride hexahydrate (15.2 g, 50 mmole) to yield [Y(thd)$_3$(H$_2$O)]$_n$ and [Tb(thd)$_3$(H$_2$O)]$_n$.

The [Y(thd)$_3$(H$_2$O)]$_n$ (28.8 g, 45 mmole) and [Tb(thd)$_3$(H$_2$O)]$_n$ (32.6 g, 45 mmole) are dissolved with warming in 200 ml of hexane, triglyme (8 g, 45 mmole) is added and the solution stirred at room temperature for 1 hour. It is then set stripped to an oil and set aside at 20° C. to crystallise.

Yield is 51 g, 82% of colourless air stable crystals.

Melting point 88°–90° C.

Microanalysis Found: C, 58.6; H, 8.9. Calcd.$YTbC_{74}H_{132}O_{16}$, C, 58.3; H, 8.7%.

$^1$H NMR in $C_6D_6$ at 270 MHz: δ–0.84 (s, $CH_3$), δ0.1 (s, br, $OCH_3$), δ1.19 (s, $CH_3$), δ7.3 (s, $OCH_2$-c+b), δ9.12 (s, $OCH_2$-a), δ5.44 (s, CH). Integral of thd:triglyme is 6:1.

Freezing point depression in benzene yields a molecular weight of 1440±60 (calc. 1526).

9. LANTHANUM TRIS-THD TRIGLYME
[La(thd)$_3$(triglyme)]—an example of a type I compound.

The first part of the preparation employs a similar method to example 1, to yield [La(thd)$_3$(H$_2$O)]$_n$.

The [La(thd)$_3$(H$_2$O)]$_n$ (20 g, 28 mmole) is dissolved with warming in 200 ml of hexane, triglyme (5.0 g, 28 mmole) is added and the solution stirred at room temperature for 1 hour. It is then set stripped to an oil and set aside at 20° C. to crystallise.

Yield is 20.5 g, 82% of pale-yellow air stable crystals.

Melting point 80°–83° C.

Microanalysis Found: C, 57.0; H, 8.9. Calcd. $LaC_{41}H_{75}O_{10}$, C, 56.8; H, 8.7%.

Infrared spectrometry (Nujol ν cm$^{-1}$): 1608 (s), 1586 (s), 1575(s), 1536(s), 1504 (s), 1451(s), 1417(s), 1388(m), 1358(s), 1137(s), 403(w).

$^1$H NMR in $C_6D_6$ at 270 MHz: δ1.19 (s, $CH_3$), δ3.22 (s, $OCH_3$), δ3.31 (s, $OCH_2$-c), δ3.57 (s, $OCH_2$-b), δ3.69 (s, $OCH_2$-a), δ5.82 (s, CH). Integral of thd:triglyme is 3:1.

Freezing point depression in benzene yields a molecular weight of 880±40 (calc. 866).

10. LANTHANUM TRIS-THD TETRAGLYME
[La(thd)$_3$(tetraglyme)]—an example of a type I compound.

Sodium hydroxide (11 g, 275 mmole) is dissolved in 75 ml methanol and stirred into a solution of thdH (50.6 g, 275 mmole) in 75 ml methanol. Then lanthanum chloride heptahydrate (34 g, 91 mmole) is dissolved in 100 ml warm methanol and added portionwise with stirring to the thdNa solution. After completing the addition the solution is stirred for 10 minutes and then poured with vigorous stirring into 1 liter of water. The precipitated product is immediately filtered off, washed on the filter with water, turned into 100 ml hexane and warmed to dissolve. The organic solution is separated from residual water and insolubles, stripped until solid begins to appear then set aside to crystallise. The product is filtered and vacuum dried as [La(thd)$_3$(H$_2$O)]$_n$.

The [La(thd)$_3$(H$_2$O)]$_n$ (57 g, 82 mmole) is dissolved with warming in 250 ml of hexane, tetraglyme (18.2 g, 82 mmole) is added and the solution stirred at room temperature for 1 hour. It is then set stripped to an oil and set aside at 20° C. to crystallise.

Yield is 75 g, 90% of pale yellow air stable crystals.

Melting point 41°–44° C.

Microanalysis Found: C, 57.0; H, 8.5. Calculated, C, 56.7; H, 8.7%.

$^1$H NMR in C$_6$D$_6$ at 270 MHz: δ1.18 (s, CH$_3$), δ3.09 (s, CH$_3$), δ3.26 (s, OCH$_2$-d), δ3.41 (s, OCH$_2$-c), δ3.43 (s, OCH$_2$-b), δ0.46 (s, OCH$_2$-a), δ5.74 (s, CH). Integral of thd:tetraglyme is 3:1.

Freezing point depression in benzene yields a molecular weight of 865±60 (calc. 911).

Figure 9A:
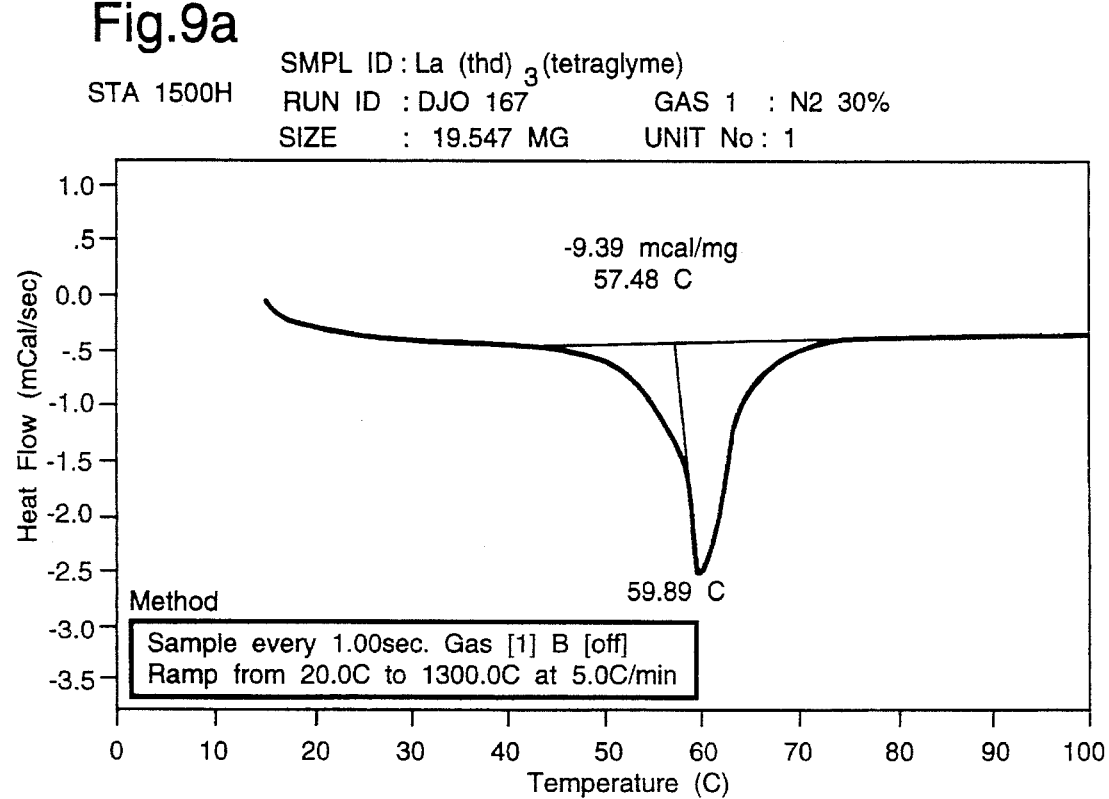
FIGS. 9–15 are thermogravimetric charts showing properties such as melting and evaporation of examples of compounds claimed.
Figure 9B:
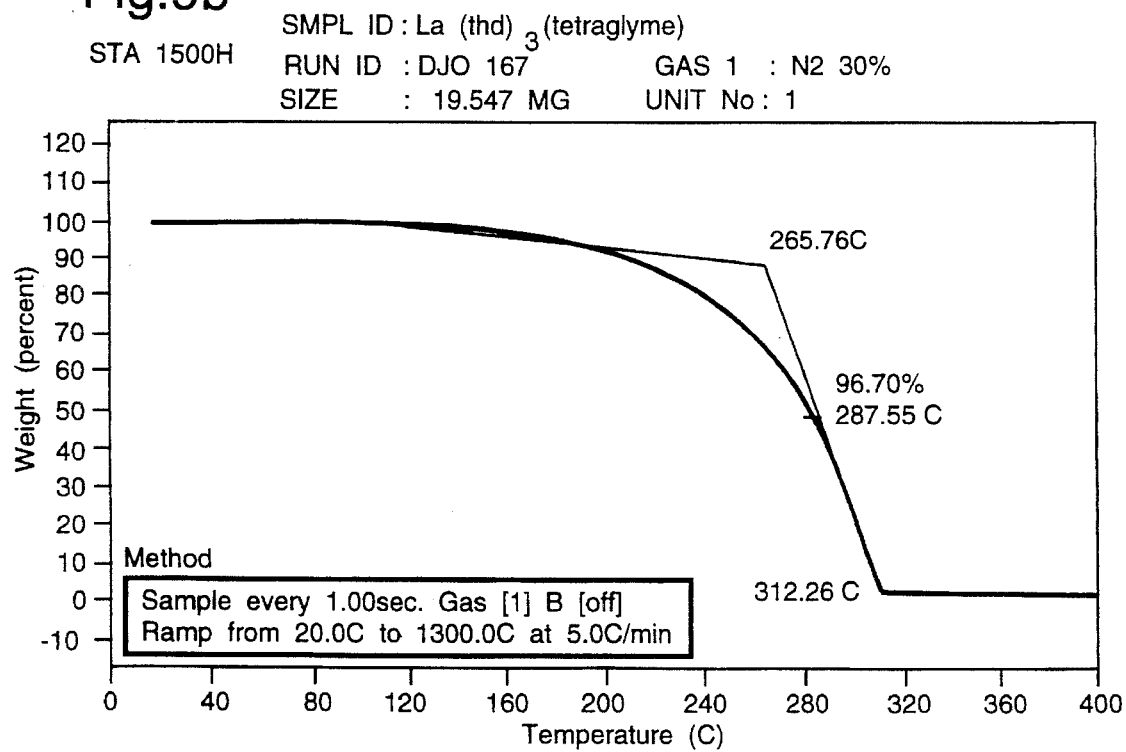

Differential scanning analysis and thermogravimetric analysis see FIGS. 9a and 9b.

X-ray crystal structure—FIG. 1.

11. LANTHANUM TRIS-HFA HEPTAGLYME [(La(hfa)$_3$)$_2$(heptaglyme)]—an example of a type II compound.

The [La(hfa)$_3$]$_n$ was prepared by a similar method to that described in example 2. The [La(hfa)$_3$]$_2$ (10 g, 14.1 mmole) is dissolved with warming in 200 ml of hexane, heptaglyme (5.0 g, 14.1 mmole) is added and the solution stirred at room temperature for 1 hour. It is then stripped to an oil and set aside at 20° C. to crystallise.

Yield is 9.2 g, 61% of colourless air stable crystals.

Melting point 57°–60° C.

Microanalysis Found: C, 26.7; H, 2.3. Calcd. La$_2$C$_{46}$H$_{40}$O$_{20}$F$_{36}$, C, 29.5; H, 2.1%.

Infrared spectrometry (Nujol ν cm$^{-1}$): 1590(m), 1574(s), 1530(s), 1502 (s), 1486(s), 1420(s), 1343(m), 1230(m), 1221(s),1178(s), 1134(s), 405(w).

$^1$H NMR in C$_6$D$_6$ at 270 MHz: δ3.04 (s, OCH$_3$), δ3.17 (m, OCH$_2$-e+f), δ3.29 (m, OCH$_2$-c+d), δ3.41 (s, OCH$_2$-b), δ3.44 (s, OCH$_2$-a), δ5.90 (s, CH). Integral of hfa:heptaglyme is 6:1.

Freezing point depression in benzene yields a molecular weight of 1830±90 (calc. 1874).

12. LANTHANUM TRIS-ACAC TETRAGLYME [La(acac)$_3$(tetraglyme)]—an example of a type I compound.

The [La(acac)$_3$]$_n$ was prepared by a similar method to that described in example 3. The [La(acac)$_3$]$_2$ (3 g, 6.6 mmole) is dissolved with warming in 50 ml of hexane, tetraglyme (1.5 g, 6.6 mmole) is added and the solution stirred at room temperature for 1 hour. It is then stripped to an oil and set aside at 20° C. to crystallise.

Yield is 2.55 g, 56% of colourless air stable crystals.

Melting point decomp >250° C.

Microanalysis Found: C, 45.8; H, 6.7. Calcd. LaC$_{25}$H$_{43}$O$_{11}$, C, 45.6; H, 6.5%.

Infrared spectrometry (Nujol ν cm$^{-1}$): 1591(m), 1572(s), 1532(s), 1504 (s), 1488(s), 1422(s), 1344(m), 1232(m), 1220(s), 1176(s), 1135(s), 404(w).

$^1$H NMR in CDCl$_3$ at 270 MHz: δ0.98 (s, CH$_3$), δ3.06 (s, OCH$_3$), δ3.20 (s, OCH$_2$-d), δ3.42 (m, OCH$_2$-c), δ3.47 (s, OCH$_2$-b), δ3.62 (s, OCH$_2$-a), δ5.83 (s, CH). Integral of acac:tetraglyme is 3:1.

13. LANTHANUM-THULIUM TRIS-THD TRIGLYME [LaTm(thd)$_6$(triglyme)]—an example of a t@DEdDGDIDK^F δ1.22 (s, CH$_3$), δ5.81 (s, CH$_{La}$), δ6.35 (s, CH$_{Tm}$), δ7.84 (s, OCH$_2$-c+b), δ14.02 (s, OCH$_2$-a). Integral of thd:triglyme is 6:1.

Sublimation behaviour: This complex remains intact on high vacuum sublimation and sublimes in near quantitative yield in the range 110°–135° C.

Freezing point depression in benzene yields a molecular weight of 1520±85 (calc. 1584).

14. CERIUM TRIS-THD DIMETHOXYETHANE [Ce(thd)$_3$(dme)]— an example of a type I compound.

Sodium hydroxide (11 g, 275 mmole) is dissolved in 50 ml of 95% ethanol and stirred into a solution of thdH (50.6 g, 275 mmole) in 75 ml methanol. Then cerium chloride heptahydrate (34.3 g, 91 mmole) and 1.2 equivalents of dimethoxyethane (dme) was dissolved in 50 ml of 50% ethanol and added portionwise with stirring to the thdNa solution. After completing the addition the solution is stirred for 10 minutes and the crude product precipitates out as a pale-brown solid. This was recrystallised from hot chloroform to produce a pale-brown crystalline solid.

Yield is 24 g, 75% of pale-brown air stable crystals.

Melting point: Does not melt below 250° C.

Microanalysis Found: C, 57.0; H, 9.1. Calcd. CeC$_{37}$H$_{69}$O$_8$, C, 56.9; H, 8.8%.

$^1$H NMR in CDCl$_3$ at 270 MHz: δ1.17 (s, CH$_3$), δ3.06 (s, OCH$_3$), δ3.22 (s, OCH$_2$), δ5.83 (s, CH). Integral of thd:dme is 3:1

Freezing point depression in benzene yields a molecular weight of 760±35 (calc. 781).

Figure 8:
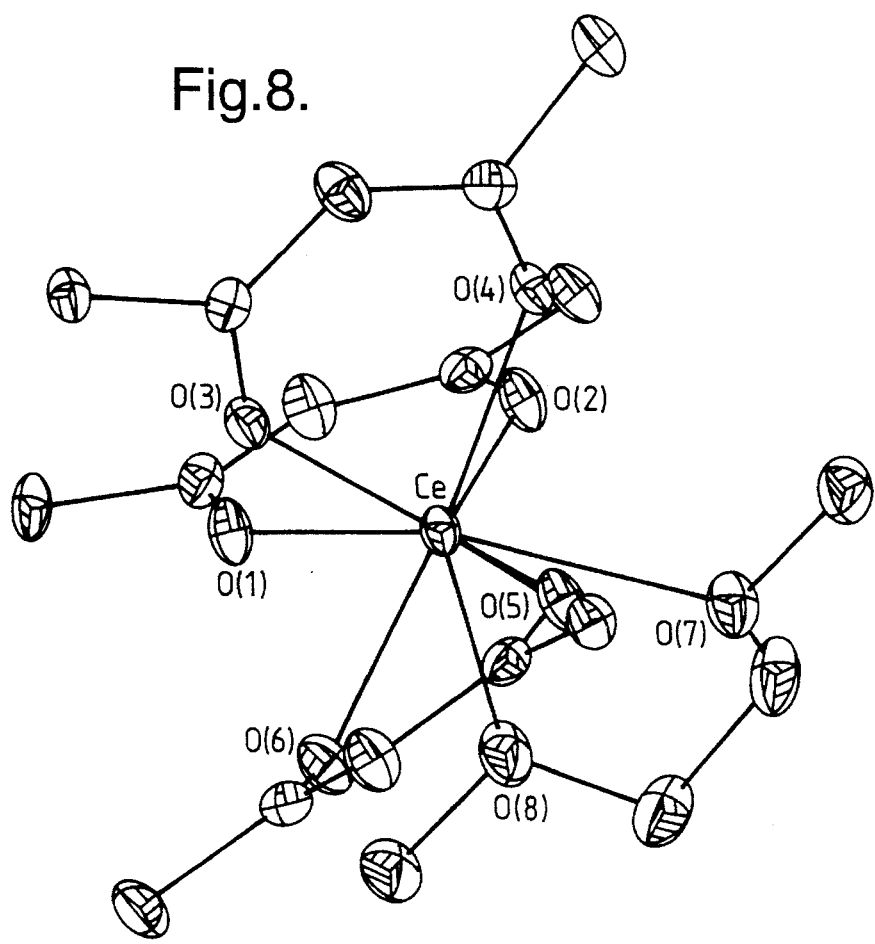
FIG. 8 [Ce(thd)$_3$(dme)]—example of a type I compound, see Example 14.

X-ray crystal structure—FIG. 8.

15. CERIUM TRIS-THD TETRAMETHYLETHYLENEDIAMINE [Ce(thd)$_3$(TMEDA)]—an example of a type I compound.

The preparation is identical to that used in example 14, except for the addition of 1.2 equivalents of tetramethylethylenediamine (tmeda) to the ethanolic cerium chloride solution to yield a pale-brown solid. This was recrystallised from hot chloroform to produce a pale-brown crystalline solid.

Yield is 33 g, 79% of pale-brown air stable crystals.

Melting point: 190°–193° C.

Microanalysis Found: C, 58.1; H, 9.4. Calcd. CeC$_{39}$H$_{75}$O$_6$N$_2$, C, 58.0; H, 9.3%.

$^1$H NMR in CDCl$_3$ at 270 MHz: δ1.18 (s, CH$_3$), δ2.07 (s, NMe$_2$), δ3.14 (s, NCH$_2$), δ5.82 (s, CH). Intergral of thd:tmeda is 3:1.

Freezing point depression in benzene yields a molecular weight of 780±40 (calc. 807).

16. CERIUM TRIS-THD TRIGLYME [Ce(thd)$_3$(triglyme)]—an example of a type I compound.

The preparation is identical to that used in example 14, except for the addition of 1.2 equivalents of triglyme to the ethanolic cerium chloride solution to yield a pale-brown solid. This was recrystallised from hot chloroform to produce a brown crystalline solid.

Yield is 33 g, 79% of brown air stable crystals.

Melting point: 90°–96° C. but possibly dissolving in liberated glyme.

Microanalysis Found: C, 57.0; H, 9.2. Calcd. CeC$_{41}$H$_{77}$O$_{10}$, C, 56.6; H, 8.9%.

$^1$H NMR in CDCl$_3$ at 270 MHz: δ1.22 (s, CH$_3$), δ3.22 (s, OCH$_3$), δ3.30 (s, OCH$_2$-c), δ3.56 (s, OCH$_2$-b), δ3.68 (s, OCH$_2$-a), δ5.8s (s, CH). Intergral of thd:triglyme is 3:1

Freezing point depression in benzene yields a molecular weight of 845±50 (calc. 869).

17. PRASEODYMIUM TRIS-THD TRIGLYME [Pr(thd)$_3$(triglyme)][(Pr(thd)$_3$)$_2$(triglyme)]—an example of a mixed type I/II compound.

The first part of the preparation employs a similar method to example 1, the quantities being sodium hydroxide (12 g, 300 mmole), thdH (55.2 g, 300 mmole) and praseodymium chloride hexahydrate (29.5 g, 100 mmole) to yield [Pr(thd)$_3$(H$_2$O)]$_n$.

The [Pr(thd)$_3$(H$_2$O)]$_n$ (55.6 g, 90 mmole) was dissolved with warming in 250 ml of hexane, triglyme (8 g, 45 mole)

is added and the solution stirred at room temperature for 1 hour. It is then stripped to an oil and set aside at 20° C. to crystallise.

Yield is 61 g, 82% of pale green air stable crystals.

Melting point 74°–77° C.

Microanalysis Found: C, 56.8; H, 8.6. Calcd., C, 56.7; H, 8.6%.

Freezing point depression in benzene yields a molecular weight of 1470±75 (calc. 1519).

Figure 13A:
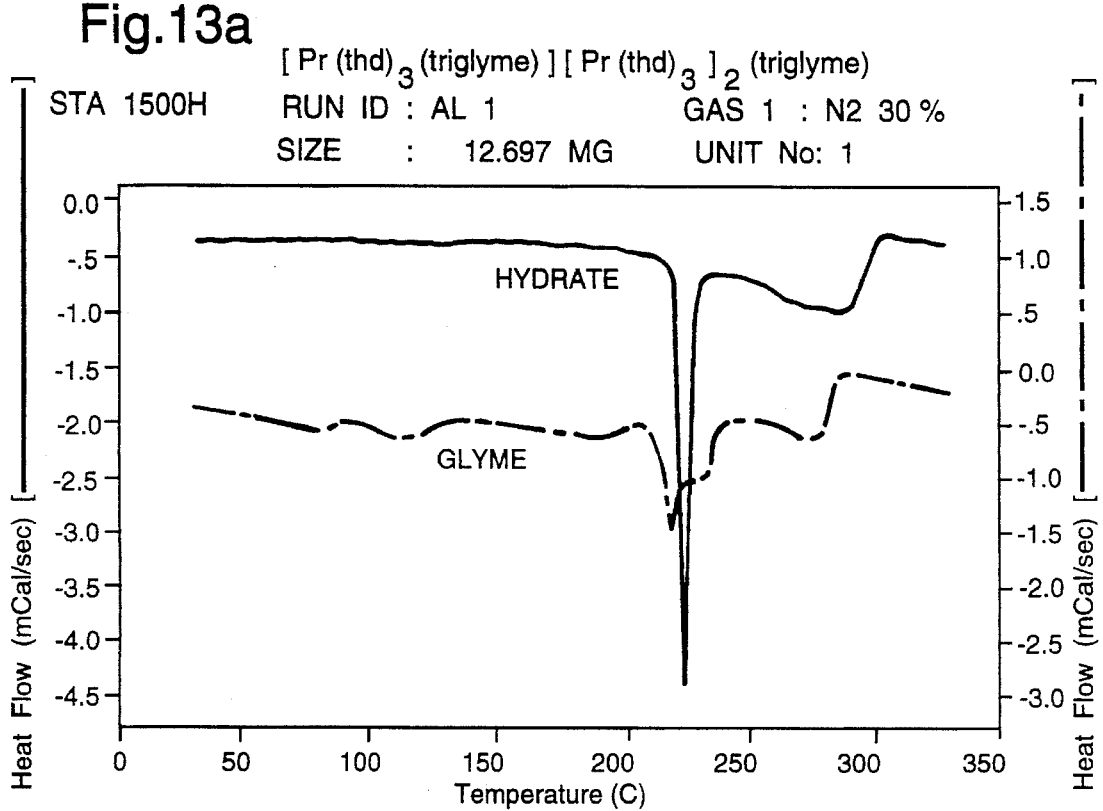
Figure 13B:
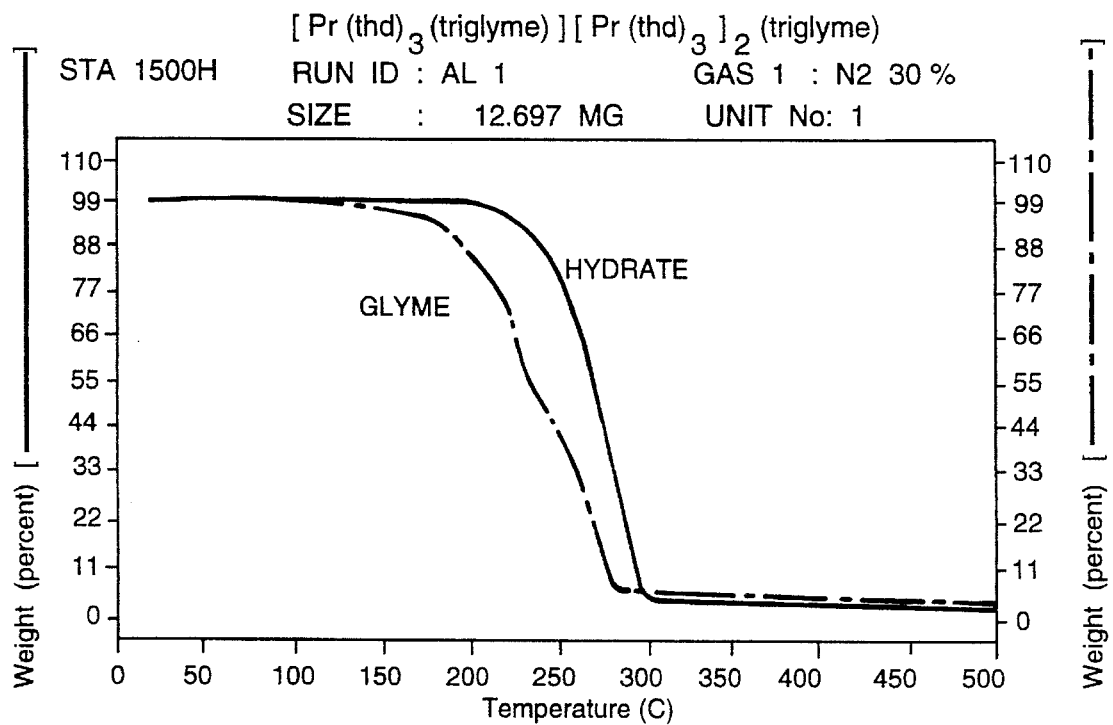
Figure 14A:
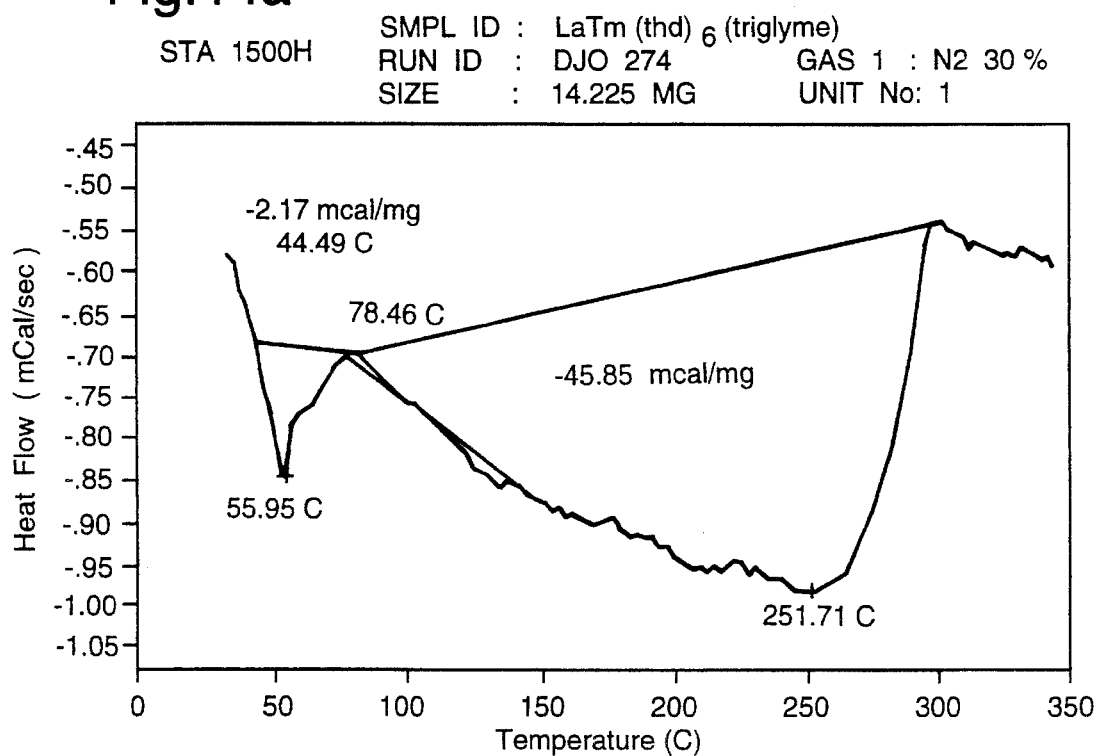
Figure 14B:
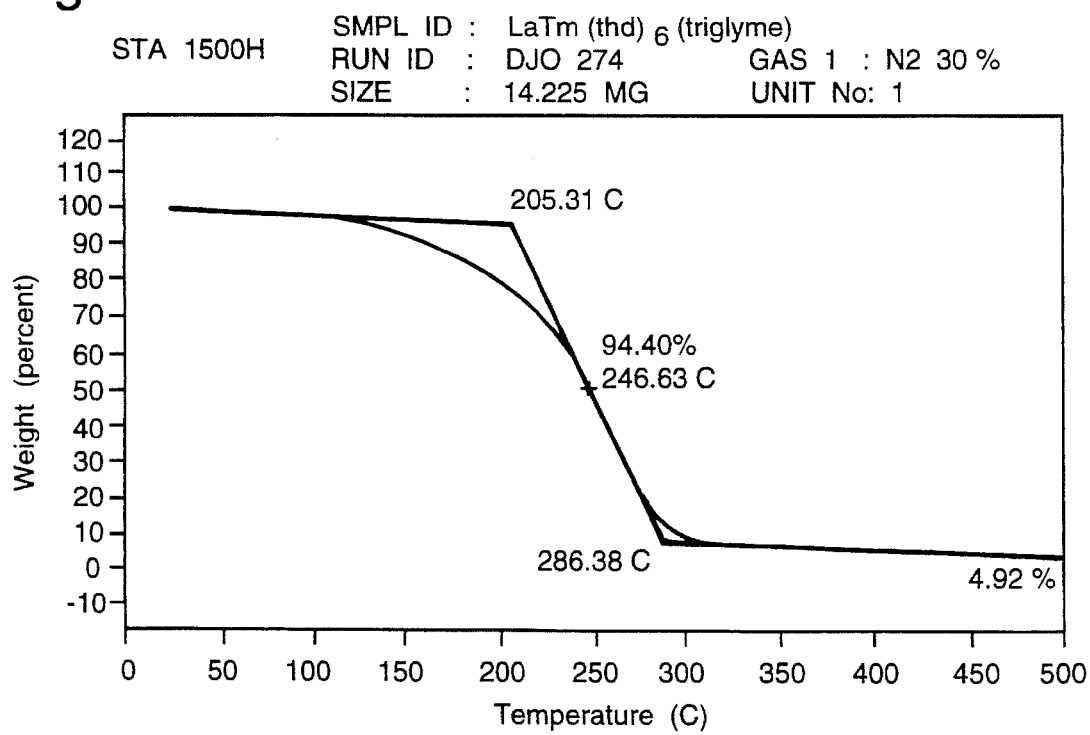
Figure 15A:
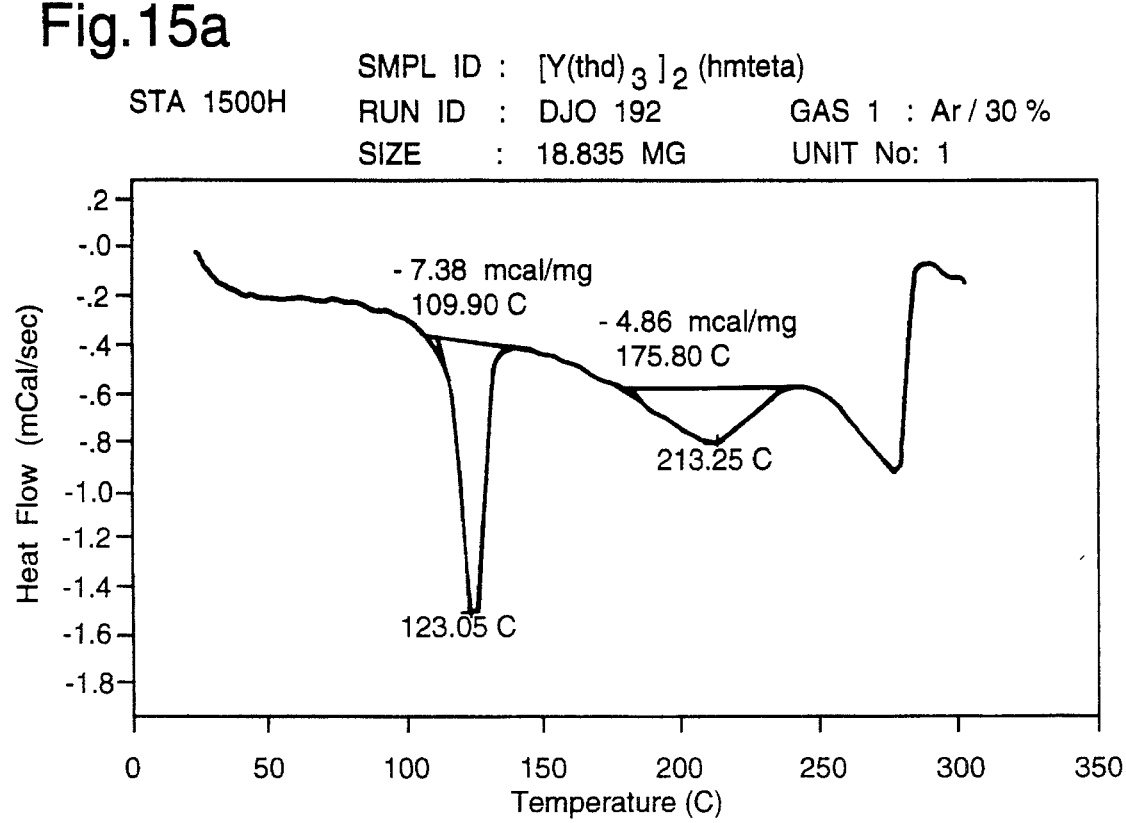
Figure 15B:
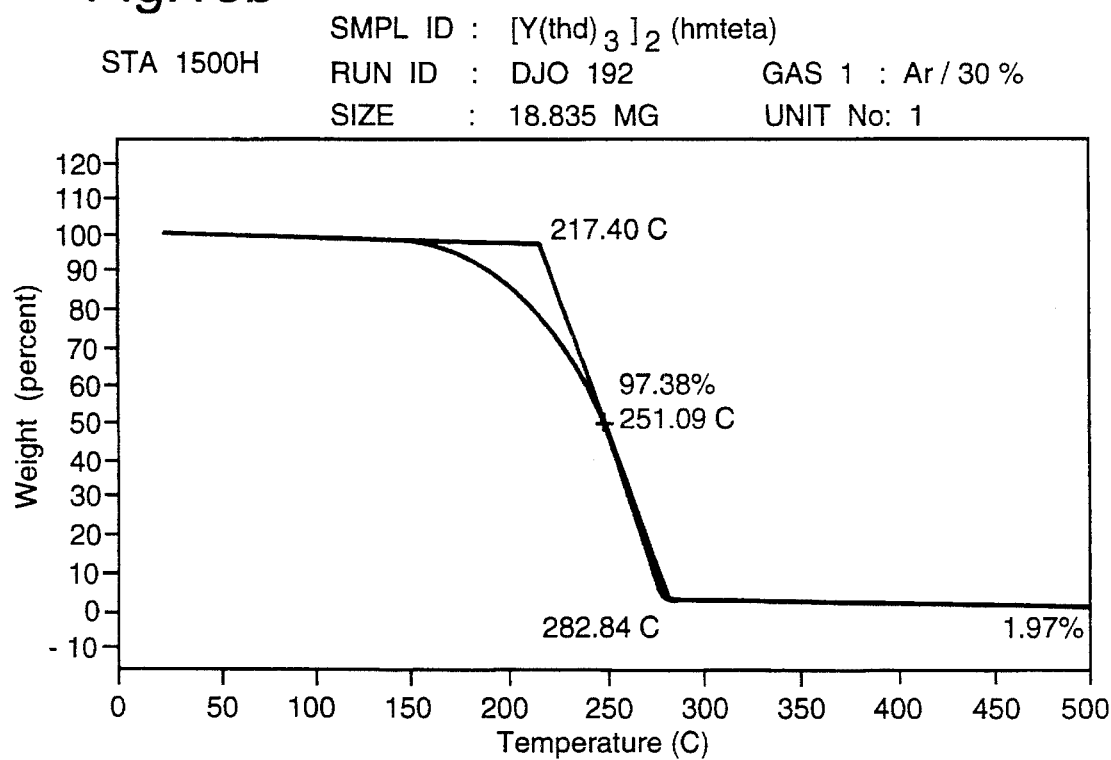

Differential scanning analysis and thermogravimetric analysis see FIGS. 13a and 13b.

Figure 5:
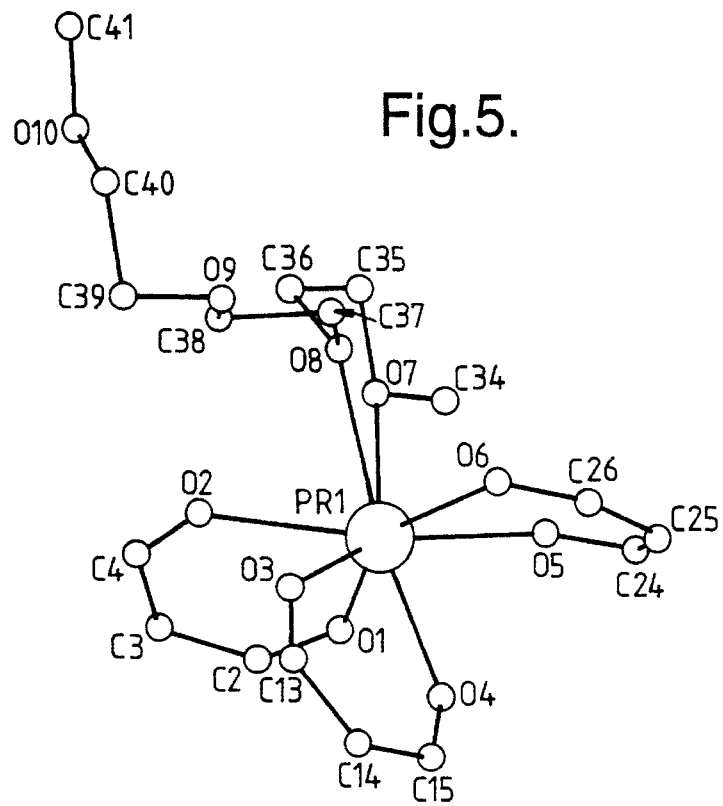
Figure 5:
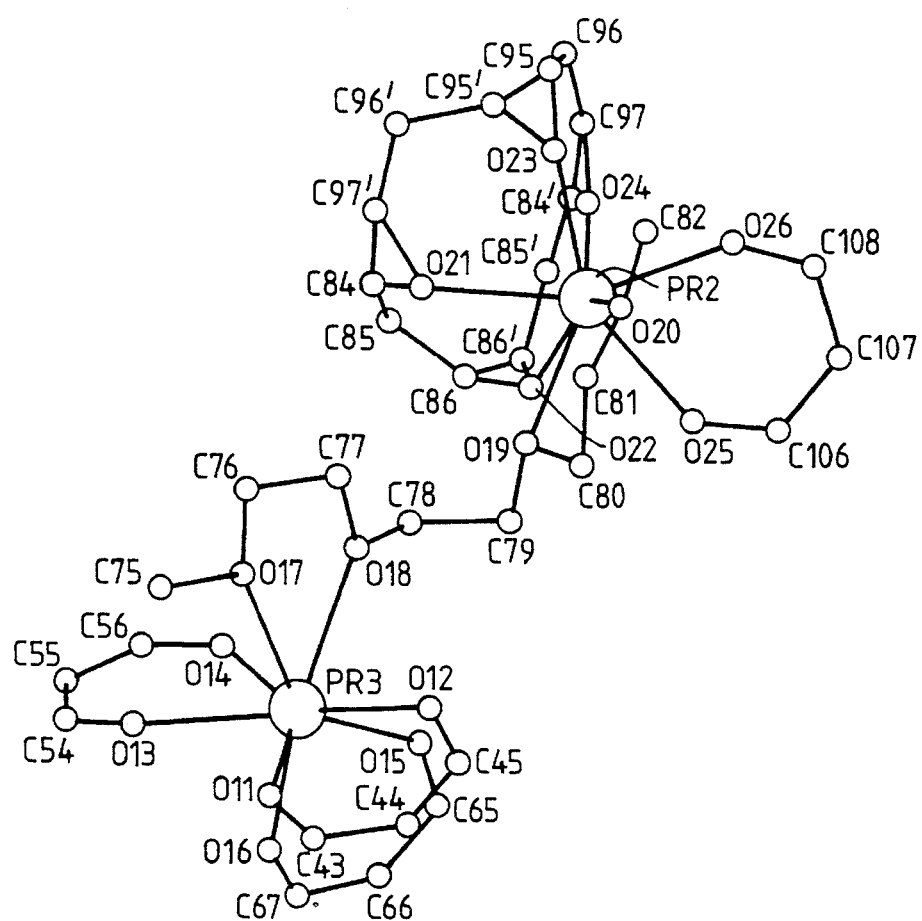

X-ray crystal structure—FIG. 5.

18. PRASEODYMIUM TRIS-THD TETRAGLYME [Pr(thd)$_3$(tetraglyme)]—an example of a type I compound.

The preparation of [Pr(thd)$_3$(H$_2$O)]$_n$ is similar to the method used for example 1. The [Pr(thd)$_3$(H$_2$O)]$_n$ (60 g, 85 mmole) was dissolved with warming in 200 ml of hexane, tetraglyme (9.3 g, 42 mmole) is added and the solution stirred at room temperature for 1 hour. It is then stripped to an oil and set aside at 20° C. to crystallise.

Yield is 63 g, 91% of pale green air stable crystals.

Melting point 83°–86° C.

Microanalysis Found: C, 56.7; H, 8.9. Calcd. PrC$_{43}$H$_{79}$O$_{11}$, C, 56.6; H, 8.7%.

Infrared spectrometry (Nujol ν cm$^{-1}$): 1607(m), 1587(s), 1573(m), 1538(s), 1502 (m), 1450(s), 1423(m), 1383(s), 1354(m), 1140(s), 402(w).

Freezing point depression in benzene yields a molecular weight of 875±44 (calc. 912).

19. PRASEODYMIUM TRIS-THD HMTETA [Pr(thd)$_3$(HMTETA)][(Pr(thd)$_3$)$_2$(HMTETA)]—an example of a mixed type I/II compound.

The preparation of [Pr(thd)$_3$(H$_2$O)]$_n$ is similar to the method used for example 1. The [Pr(thd)$_3$(H$_2$O)]$_n$ (90 g, 127.5 mmole) was dissolved with warming in 300 ml of hexane, hmteta (29.25 g, 127.5 mmole) is added and the solution stirred at room temperature for 1 hour. It is then stripped to an oil and set aside at 20° C. to crystallise.

Yield is 160.5 g, 76% of pale green air stable crystals.

Melting point: 150°–152° C.

Microanalysis Found: C, 61.4; H, 9.7. Calcd. Pr$_3$C$_{123}$H$_{231}$O$_{18}$N$_8$, C, 61.8; H, 9.7%.

Freezing point depression in benzene yields a molecular weight of 875±44 (calc. 912).

Mass Spectrometry (EI$^+$): 1469 [Pr$_2$(thd)$_6$(hmteta)]$^+$ (3%), 1286 [Pr$_2$(thd)$_5$(hmteta)]$^+$ (2%), 920 [Pr(thd)$_3$(hmteta)]$^+$ (8%), 690 [Pr(thd)$_3$]$^+$ (70%).

20. PRASEODYMIUM TRIS-HFA DIGLYME [Pr(hfa)$_3$(diglyme)]$_2$—an example of a type III compound.

The preparation of [Pr(hfa)$_3$(H$_2$O)]$_n$ is similar to the method used for example 1. The [Pr(hfa)$_3$(H$_2$O)]$_n$ (100 g, 128 mmole) was dissolved with warming in 500 ml of hexane, diglyme (17.1 g, 128 mmole) is added and the solution stirred at room temperature for 1 hour. It is then stripped to an oil and set aside at 20° C. to crystallise.

Yield is 103 g, 87% of green air stable crystals.

Melting point 85°–88° C.

Microanalysis Found: C, 28.3; H, 1.8. Calcd. PrC$_{21}$H$_{17}$O$_9$F$_{18}$, C, 28.1; H, 1.7%.

Freezing point depression in benzene yields a molecular weight of 875±44 (calc. 912).

Mass Spectrometry (EI$^+$): 896 [Pr(hfa)$_3$(diglyme)]$^+$ (14%), 762 [Pr(hfa)$_3$]$^+$ (71%) and lower mass ions containing hfa fragments.

21. PRASEODYMIUM TRIS-HFA PMDETA [Pr(hfa)$_3$(pmdeta)]—an example of a type I compound.

The preparation of [Pr(hfa)$_3$(H$_2$O)]$_n$ is similar to the method used for example 1. The [Pr(hfa)$_3$(H$_2$O)]$_n$ (75 g, 96 mmole) was dissolved with warming in 250 ml of hexane, pmdeta (16.5 g, 96 mmole) is added and the solution stirred at room temperature for 1 hour. It is then stripped to an oil and set aside at 20° C. to crystallise.

Yield is 62 g, 68% of light green air stable crystals.

Melting point >250° C.

Microanalysis Found: C, 31.0; H, 2.9. Calcd. PrC$_{24}$H$_{26}$O$_6$F$_{18}$N$_3$, C, 30.8; H, 2.8%.

Mass Spectrometry (EI$^+$): 935 [Pr(hfa)$_3$(pmdeta)]$^+$ (18%), 762 [Pr(hfa)$_3$]$^+$ (64%) and lower mass ions containing hfa fragments.

22. NEODYMIUM TRIS-THD DIGLYME [Nd(thd)$_3$(diglyme)]$_2$—an example of a type III compound.

The preparation of [Nd(thd)$_3$(H$_2$O)]$_n$ is similar to the method used for example 1. The [Nd(thd)$_3$(H$_2$O)]$_n$ (12.5 g, 17.6 mmole) is dissolved with warming in 250 ml of hexane, diglyme (2.35 g, 17.6 mmole) is added and the solution stirred at room temperature for 1 hour. It is then stripped to an oil and set aside at 20° C. to crystallise.

Yield is 10.8 g, 73% of pink air stable crystals.

Melting point 111°–113° C.

Microanalysis Found: C, 56.8; H, 8.4. Calcd.NdC$_{39}$H$_{39}$O$_6$, C, 56.6; H, 8.3%.

$^1$H NMR in C$_6$D$_6$ at 270 MHz: δ–1.22 (s, br, CH$_3$), δ0.13 (s,br, OCH$_3$), δ1.32 (s, CH), δ7.14 (s, br, OCH$_2$-b), δ9.36 (s, br, OCH$_2$-a). Integral of thd:diglyme is 3:1.

Freezing point depression in benzene yields a molecular weight of 790±40 (calc. 827).

23. NEODYMIUM TRIS-THD TRIGLYME [{Nd(thd)$_3$}$_2$(triglyme)]—an example of a type II compound.

The preparation of [Nd(thd)$_3$(H$_2$O)]$_n$ is similar to the method used for example 1. The [Nd(thd)$_3$(H$_2$O)]$_n$ (25 g, 35.2 mmole) is dissolved with warming in 250 ml of hexane, triglyme (6.3 g, 35.2 mmole) is added and the solution stirred at room temperature for 1 hour. It is then stripped to an oil and set aside at 20° C. to crystallise.

Yield is 19.3 g, 62% of pink air stable crystals.

Melting point 74°–77° C.

Microanalysis Found: C, 57.2; H, 8.6. Calcd. Nd$_2$C$_{74}$H$_{132}$O$_{16}$, C, 56.8; H, 8.4%.

Infrared spectrometry (Nujol ν cm$^{-1}$): 1604(s), 1583(m), 1572(s), 1534(s), 1503 (m), 1447(m), 1418(s), 1393(m), 1356(s), 1135(s), 407(w).

$^1$H NMR in C$_6$D$_6$ at 270 MHz: δ–1.74 (s, br,CH$_3$), δ–0.87 (s, OCH$_3$), δ8.22 (s, OCH$_2$-c), δ9.04 (s, OCH$_2$-b), δ11.78 (s, OCH$_2$-a). Integral of thd:triglyme is 6:1. Note the CH signal is not observed.

Freezing point depression in benzene yields a molecular weight of 1525±73 (calc. 1564).

24. NEODYMIUM TRIS-Ph$_2$acac TETRAGLYME [Nd(Ph$_2$acac)$_3$(tetraglyme)]—an example of a type I compound.

The preparation of [Nd(Ph$_2$acac)$_3$]$_n$ is similar to the method used for example 3. The quantities used are [Nd(hmdz)$_3$]$_n$ (15 g, 24.0 mmole), Ph$_2$acacH (16.1 g, 72 mmole) and tetraglyme (5.3 g, 24 mmole).

Yield is 22.8 g, 91% of pink air stable crystals.

Melting point >250° C..

Microanalysis Found: C, 64.2; H, 5.5. Calcd. $NdC_{55}H_{55}O_{11}$, C, 63.8; H, 5.3%.

$^1$H NMR in $CDCl_3$ at 270 MHz: $\delta 0.12$ (s, br, $OCH_3$), $\delta 2.14$ (s, br, Ph), $\delta 2.66$ (s,br, Ph), $\delta 3.44$ (s, br, Ph) $\delta 7.60$ (s, br, $OCH_2$-c), $\delta 8.83$ (s,br, $OCH_2$-b), $\delta 10.45$ (s, br, $OCH_2$-a). Integral of $Ph_2acac$:tetraglyme is 6:1. Note the CH signal is not observed.

25. SAMARIUM TRIS-THD DIMETHOXYETHANE [$Sm(thd)_3(DME)$]— an example of a type I compound.

The preparation is similar to that used in example 14, except for the addition of 1.1 equivalents of dimethoxyethane (dme) (1.92 g 21.1 mmole) to the ethanolic samrium chloride solution (7.0 g 19.2 mole), which is subsequently added to the thdNa solution (11.9 ml 57.6 mmole) to yield a pale-yellow solution. This was then stripped to an oil and set aside at 20° C. to crystallise.

Yield is 10.7 g, 71% of pale-yellow air stable crystals.

Melting point: 96°–98° C.

Microanalysis Found: C, 56.6; H, 8.9. Calcd. $SmC_{37}H_{69}O_8$, C, 56.2; H, 8.7%.

Mass Spectrometry ($EI^+$): 790 [$Sm(thd)_3(dme)$]$^+$ (3%), 700 [$Sm(thd)_3$]$^+$ (53%).

26. SAMARIUM TRIS-HFA TETRAGLYME [{$Sm(hfa)_3$}$_2$(tetraglyme)]—an example of a type II compound.

The preparation of [$Sm(hfa)_3(H_2O)$]$_n$ is similar to the method used for example 1. The [$Sm(hfa)_3(H_2O)$]$_n$ (3.0 g, 3.8 mmole) is dissolved with warming in 40 ml of hexane, tetraglyme (0.49 g, 3.8 mmole) is added and the solution stirred at room temperature for 1 hour. It is then stripped to an oil and set aside at 20° C. to crystallise.

Yield is 2.6 g, 74% of light-yellow air stable crystals.

Melting point: 90°–92° C.

Microanalysis Found: C, 27.7; H, 1.8. Calcd. $Sm_2C_{40}H_{28}O_{17}F_{36}$, C, 27.2; H, 1.6%.

Infrared spectrometry (Nujol $\nu$ cm$^{-1}$): 1611(s), 1590(m), 1575(s), 1531s, 1502(s), 1441(m), 1419(s), 1379(m), 1349(s), 1130(s), 409(w).

Freezing point depression in benzene yields a molecular weight of 1710±90 (calc. 1765).

27. SAMARIUM TRIS-ACAC HEPTAGLYME [{$Sm(thd)_3$}$_2$(heptaglyme)]—an example of a type II compound.

The preparation of [$Sm(acac)_3$]$_n$ is similar to the method used for example 3. The quantities used are [$Sm(hmdz)_3$]$_n$ (4 g, 6.03 mmole), acacH (1.8 g, 18.1 mole) and heptaglyme (2.2 g, 6.03 mole). The solution is stirred at room temperature for 1 hour and then stripped to an oil and set aside at 20° C. to crystallise.

Yield is 5.4 g, 71,1% of yellow air stable crystals.

Melting point: decomp >250° C.

Microanalysis Found: C, 44.5; H, 5.9. Calcd. $Sm_2C_{46}H_{76}O_{20}$, C, 44.2; H, 6.1%.

Mass Spectrometry ($EI^+$): 1249 [$Sm_2(acac)_6(heptaglyme)$]$^+$ (1%), 796 [$Sm_2(acac)_5$]$^+$ (61%), 700 [$Sm(thd)_3$]$^+$ (16%) and lower mass ions.

28. EUROPIUM TRIS-THD TRIGLYME [($Eu(thd)_3$)$_2$(triglyme)]—an example of a type II compound.

The first part of the preparation employs a similar method to example 1 to yield [$Eu(thd)_3(H_2O)$]$_n$. The [$Eu(thd)_3(H_2O)$]$_n$ (57.5 g, 90 mmole) is dissolved with warming in 250 ml of hexane, triglyme (8 g, 45 mmole) is added and the solution stirred at room temperature for 1 hour. It is then set stripped to an oil and set aside at 20° C. to crystallise.

Yield is 63.4 g, 97% of pale-yellow air stable crystals.

Melting point 111°–114° C.

Microanalysis Found: C, 55.8; H, 8.2. Calcd. $Eu_2C_{74}H_{132}O_{16}$, C, 55.7; H, 8.3%.

$^1$H NMR in $C_6D_6$ at 270 MHz: $\delta$–0.55 (s, br, $CH_3$), $\delta$–0.35 (s, $OCH_3$), $\delta 8.99$ (s, $OCH_2$-a), $\delta 10.26$ (s, $OCH_2$-b), $\delta 11.05$ (s, $OCH_2$-c+d). Integral of thd:triglyme is 6:1.

Freezing point depression in benzene yields a molecular weight of 1529±75 (calc. 1580).

Figure 10A:
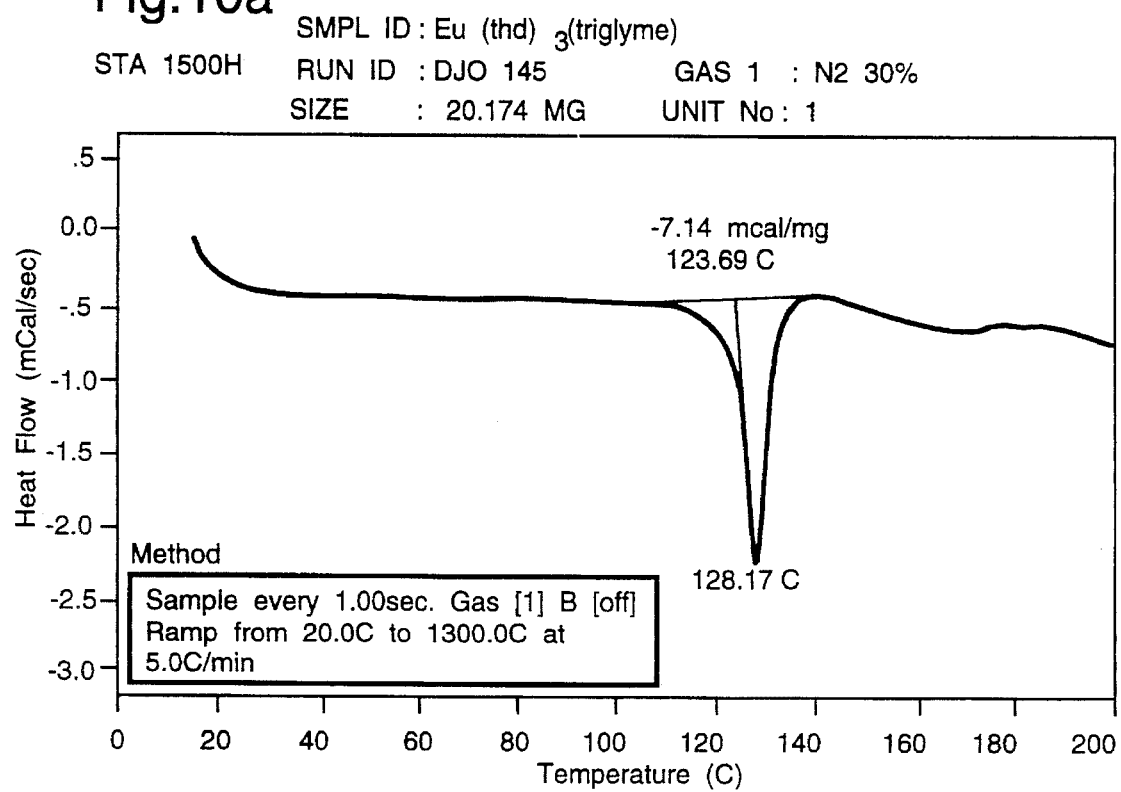
Figure 10B:
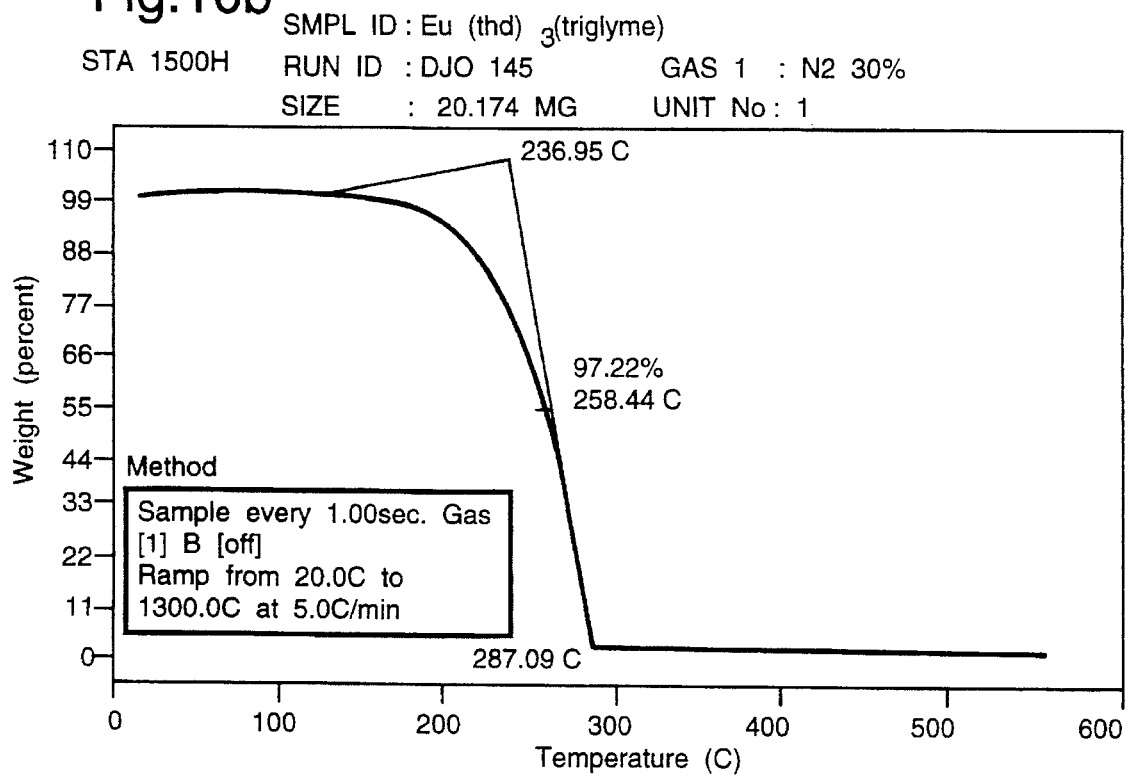
Figure 11A:
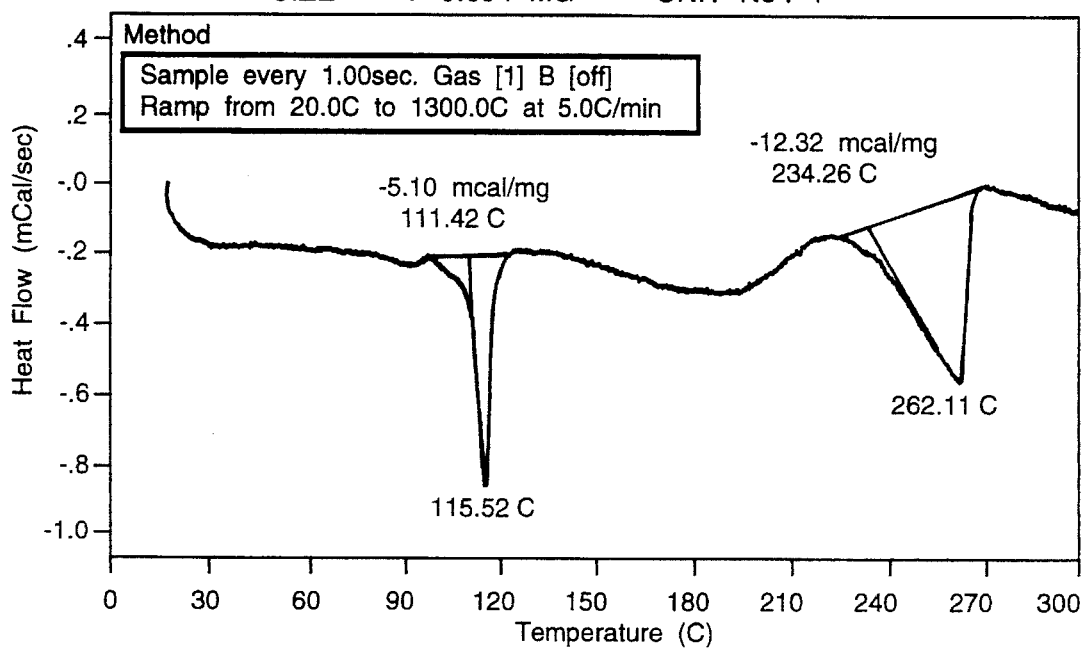
Figure 11B:
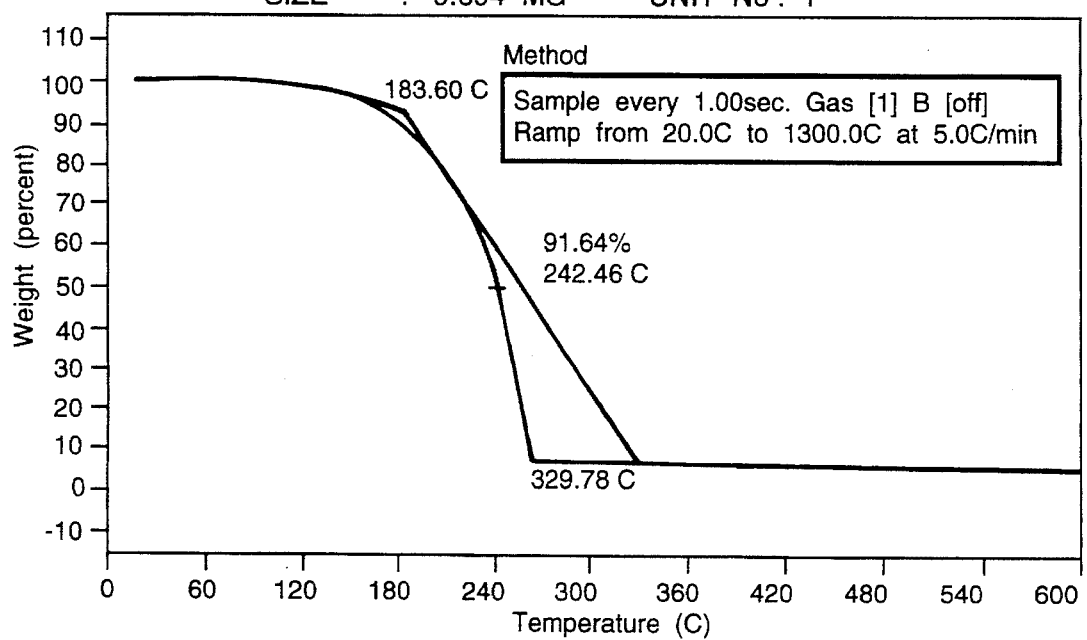

Differential scanning analysis and thermogravimetric analysis see FIGS. 10$a$ and 10$b$.

29. EUROPIUM TRIS-THD TETRAGLYME [($Eu(thd)_3$)$_2$(tetraglyme)]—an example of a type II compound.

The first part of the preparation employs a similar method to example 1 to yield [$Eu(thd)_3(H_2O)$]$_n$. The [$Eu(thd)_3(H_2O)$]$_n$ (80.0 g, 111 mmole) is dissolved with warming in 400 ml of hexane, tetraglyme (12.2 g, 55 mmole) is added and the solution stirred at room temperature for 1 hour. It is then set stripped to an oil and set aside at 20° C. to crystallise.

Yield is 79.1 g, 86% of pale-yellow air stable crystals.

Melting point 98°–100° C.

Microanalysis Found: C, 56.1; H, 8.6. Calcd. $Eu_2C_{82}H_{78}O_{20}$, C, 55.7; H, 8.3%.

$^1$H NMR in $C_6D_6$ at 270 MHz: $\delta$–1.04 (s, br, $CH_3$), $\delta 0.12$ (s, $OCH_3$), $\delta 8.36$ (s, $OCH_2$-a), $\delta 9.61$ (s, $OCH_2$-b), $\delta 12.13$ (s, $OCH_2$-c+d). Integral of thd:tetraglyme is 6:1.

Freezing point depression in benzene yields a molecular weight of 1570±78 (calc. 1624).

30. GADOLINIUM TRIS-THD DIMETHOXYETHANE [$Gd(thd)_3(dme)$]—an example of a type I compound.

The first part of the preparation employs a similar method to example 1 to yield [$Gd(thd)_3(H_2O)$]$_n$.

The [$Gd(thd)_3(H_2O)$]$_n$ (40.0 g, 55.23 mmole) is dissolved with warming in 400 ml of hexane, and the solution stirred at for 15 min. The solvent is then removed under vacuum to yield an off-white solid, which is redissolved in 50 ml of hot hexane to give the [$Gd_2(thd)_6$] as white needles.

Yield is 37.2 g, 96% of colourless air stable crystals.

Melting point 176°–178° C.

Microanalysis Found: C, 56.9; H, 8.3. Calcd. $GdC_{33}H_{57}O_6$, C, 56.1; H, 8.2%.

Infrared spectrometry (Nujol $\nu$ cm$^{-1}$): 1580(m), 1571(m), 1538(m), 1501 (m), 1403(s), 1355(vs), 1180(m), 1132(w), 475(w), 405(w).

Freezing point depression in benzene yields a molecular weight of 1380±45 (calc. 1414).

Mass Spectrometry ($EI^+$): 707 [$Gd(thd)_3$]$^+$ (1%), 651 [$Gd(thd)_2(Bu^tCOCHCO)$]$^+$ (26%), 524 [$Gd(thd)_2$]$^+$ (100%) and lower mass ions.

X-ray analysis has confirmed that the molecule is a dimer.

The [$Gd_2(thd)_6$] (10.0 g, 7.0 mmole) is dissolved with warming in 80 ml of hexane, dme (0.25 ml, 7.0 mmole) is added and the solution stirred at room temperature for 1 hour. The solution was then left for 24 hs. at –20° C. to crystallise.

Yield is 9.7 g, 95% of colourless air stable crystals.

Melting point shows evidence of dissolution in the dme ligand 117°–130° C.

Microanalysis Found: C, 55.9; H, 8.6. Calcd. $GdC_{37}H_{67}O_8$, C, 55.7; H, 8.5%.

Infrared spectrometry (Nujol ν cm$^{-1}$): 1588(s), 1575(s), 1538(s), 1505 (s), 1418(s), 1357(s), 1197(m), 1139(w), 475(w), 407(w).

Mass Spectrometry (EI$^+$): 797 [Gd(thd)$_3$(dme)] (1%), 707 [Gd(thd)$_3$]$^+$ (37%), 651 [Gd(thd)$_2$(Bu$^t$COCHCO)]$^+$ (26%), 524 [Gd(thd)$_2$]$^+$ (100%) and lower mass ions.

X-ray analysis has confirmed that the molecule is an eight coordinate monomer, [Gd(thd)$_3$(dme)].

31. GADOLINIUM TRIS-THD DIGLYME [Gd(thd)$_3$(diglyme)]$_2$—an example of a type III compound.

The [Gd(thd)$_3$]$_2$ {prepared via examples 1 and 30} (10.0 g, 7.0 mmole) is dissolved with warming in 80 ml of hexane, diglyme (1.75 ml, 14.0 mmole) is added and the solution stirred at room temperature for 1 hour. The solution was then left for 24 hs. at −20° C. to crystallise.

Yield is 9.3 g, 86% of colourless air stable crystals.

Melting point 77°–79° C.

Microanalysis Found: C, 56.0; H, 8.6. Calcd. $GdC_{39}H_{71}O_9$, C, 55.7; H, 8.5%.

Infrared spectrometry (Nujol ν cm$^{-1}$): 1577(vs), 1536(s), 1505 (vs), 1456(vs), 1376(s), 1180(m), 1139(s), 476(m), 398(w).

Mass Spectrometry (EI$^+$): 797 [Gd(thd)$_3$(dme)] (1%), 707 [Gd(thd)$_3$]$^+$ (37%), 651 [Gd(thd)$_2$(Bu$^t$COCHCO)]$^+$ (26%), 524 [Gd(thd)$_2$]$^+$ (100%) and lower mass ions.

32. GADOLINIUM TRIS-THD TRIGLYME [{Gd(thd)$_3$}$_2$(triglyme)]—an example of 8 type II compound.

The [Gd(thd)$_3$]$_2$ {prepared via examples 1 and 30} (10.0 g, 7.0 mmole) is dissolved with warming in 80 ml of hexane, triglyme (2.60 ml, 14.0 mmole) is added and the solution stirred at room temperature for 1 hour. The solvent was then removed yielding an oil, from which over a period of 24 hrs. at −20° C. colourless crystals formed.

Yield is quantitative of colourless air stable crystals.

Melting point 87°–89° C.

Microanalysis Found: C, 55.7; H, 8.2. Calcd. $Gd_2C_{74}H_{132}O_{16}$, C, 55.8; H, 8.3%.

Infrared spectrometry (Nujol ν cm$^{-1}$): 1576(s), 1537(s), 1505 (s), 1490(s), 1423(s), 1358(s), 1181(m), 1138(s), 476(m), 407(m).

Mass Spectrometry (EI$^+$): 707 [Gd(thd)$_3$]$^+$ (17%), 651 [Gd(thd)$_2$(Bu$^t$COCHCO)]$^+$ (23%), 524 [Gd(thd)$_2$]$^+$ (18%) and lower mass ions.

Freezing point depression in benzene yields a molecular weight of 1550±63 (calc. 1591).

X-ray structural analysis has confirmed the molecular formula.

33. GADOLINIUM TRIS-THD TETRAGLYME [{Gd(thd)$_3$}$_2$(tetraglyme)]— an example of a type II compound.

The [Gd(thd)$_3$]$_2$ {prepared via examples 1 and 30} (7.1 g, 5.0 mmole) is dissolved with warming in 70 ml of hexane, tetraglyme (2.22 ml, 10.0 mmole) is added and the solution stirred at room temperature for 1 hour. The solvent was then removed and the resulting oil left to crystallise.

Yield is 6.4 g 78%.

Melting point 88°–91° C.

Microanalysis Found: C, 55.5; H, 8.2. Calcd. $Gd_2C_{76}H_{136}O_{17}$, C, 55.8; H, 8.4%.

Infrared spectrometry (Nujol ν cm$^{-1}$): 1589(s), 1575(s), 1538(s), 1505 (s), 1359(s), 1181(m), 1139(s), 475(mw), 406(w).

Mass Spectrometry (EI$^+$): 707 [Gd(thd)$_3$]$^+$ (7%), 650 [Gd(thd)$_2$(Bu$^t$COCHCO)]$^+$ (42%), 524 [Gd(thd)$_2$]$^+$ (87%) and lower mass ions.

Figure 7:
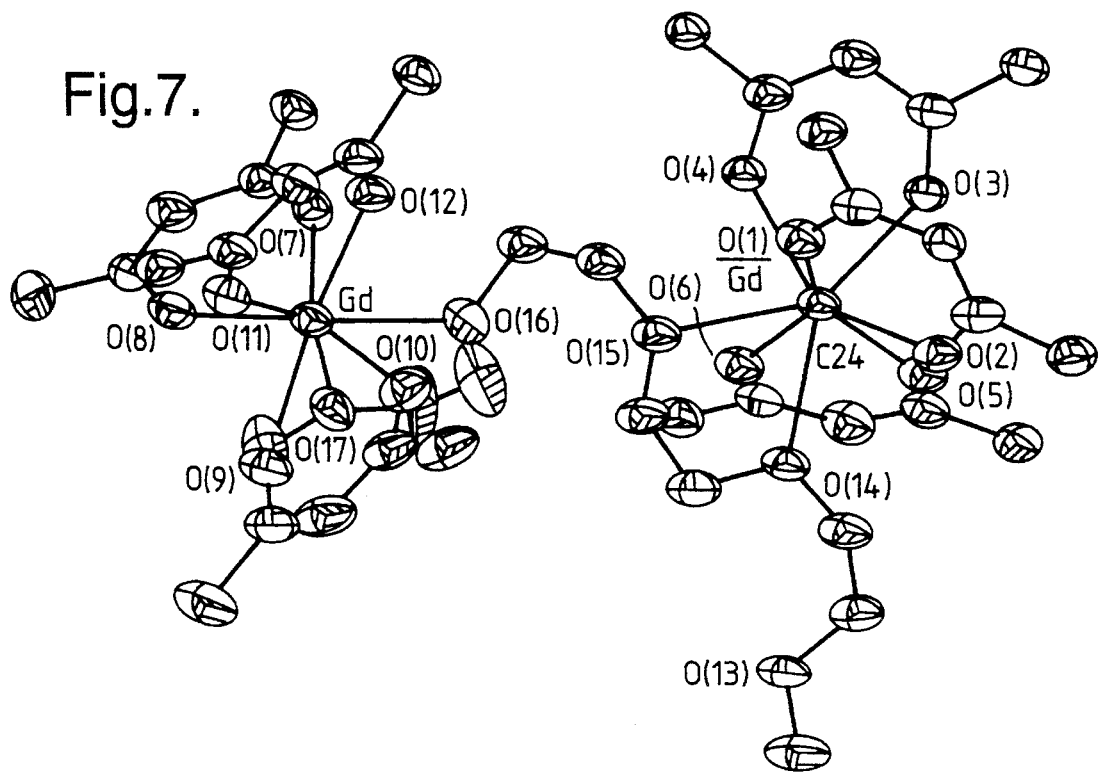

X-ray structural analysis, see FIG. 7.

34. GADOLINIUM TRIS-THD HEPTAGLYME [{Gd(thd)$_3$}$_2$(heptaglyme)]—an example of a type II compound.

The [Gd(thd)$_3$]$_2$ {prepared via examples 1 and 30} (7.1 g, 5.0 mmole) is dissolved with warming in 70 ml of hexane, heptaglyme (3.50 ml, 10.0 mmole) is added and the solution stirred at room temperature for 1 hour. The solvent was then removed and the resulting oil left to crystallise for 4 hs. at 20° C.

Yield is 8.0 g 91%.

Melting point 82°–84° C.

Microanalysis Found: C, 55.6; H, 8.4. Calcd. $Gd_2C_{82}H_{148}O_{20}$, C, 55.7; H, 8.4%.

Infrared spectrometry (Nujol ν cm$^{-1}$): 1575(s), 1538(s), 1505 (s), 1423(s), 1358(s), 1227(ms), 1180(m), 1137(s), 476(w), 405(w).

Mass Spectrometry (EI$^+$): 1509 [Gd$_2$(thd)$_6$(triglyme)]$^+$ (1%), 1354 [Gd$_2$(thd)$_5$(Bu$^t$COCHCO)]$^+$ (5%), [Gd$_2$(thd)$_5$]$^+$ (24%), and lower mass ions.

Figure 6:
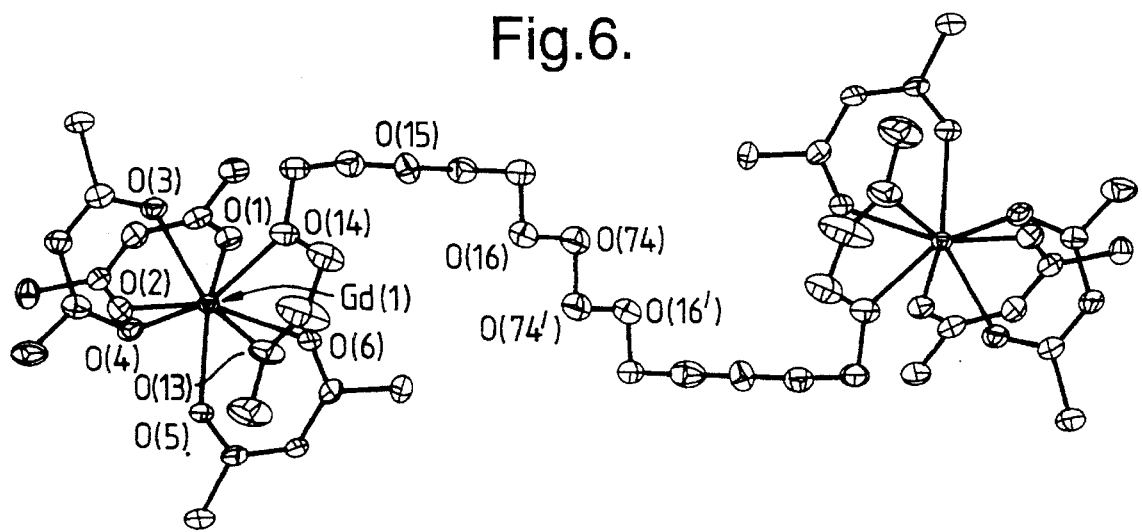

X-ray structural analysis, see FIG. 6.

35. GADOLINIUM TRIS-THD HEXAMETHYLTRIETHYLENETETRAMINE [{Gd(thd)$_3$}$_2$(hmteta)]—an example of a type II compound.

The [Gd(thd)$_3$]$_2$ {prepared via examples 1 and 30} (7.1 g, 5.0 mmole) is dissolved with warming in 70 ml of hexane, hmteta (2.3 ml, 10.0 mole) is added and the solution stirred at room temperature for 1 hour. The solvent was then removed and the resulting oil left to crystallise for 4 hs. at 20° C.

Yield is 7.0 g 84%.

Melting point 91°–93° C.

Microanalysis Found: C, 57.4; H, 8.9. Calcd. $Gd_2C_{78}H_{144}O_{12}N_4$, C, 57.0; H, 8.8%.

Infrared spectrometry (Nujol ν cm$^{-1}$): 1574(s), 1533(s), 1501 (s), 1452(s), 1371(s), 1222(m), 1176(m), 402(w).

Mass Spectrometry (EI$^+$): 1643 [Gd$_2$(thd)$_6$(hmteta)]$^+$ (1%), 1354 [Gd$_2$(thd)$_5$(Bu$^t$COCHCO)]$^+$ (5%), [Gd$_2$(thd)$_5$]$^+$ (24%), and lower mass ions.

Sublimation: Sublimes in excellent yield over the range 85°–120° C. and 1×10$^{-3}$ torr.

Freezing point depression in benzene yields a molecular weight of 1570±78 (calc. 1624).

36. GADOLINIUM TRIS-ACAC DIMETHOXYETHANE [Gd(acac)$_3$(dme)]—an example of a type I compound.

The preparation of [Gd(acac)$_3$(dme)] is similar to the method used for example 3. The quantities used are [Gd(hmdz)$_3$]$_n$ (6 g, 9.4 mmole), acacH (2.8 g, 28.2 mmole) and monoglyme (1.7 ml, 18.8 mole). The solution is stirred at room temperature for 1 hour and then stripped to an oil and set aside at 20° C. to crystallise.

Yield is 4.3 g, 83% of colourless air stable crystals.

Melting point shows evidence of dissolving in the glyme 126°–135° C.

Microanalysis Found: C, 42.1; H, 5.9. Calcd. $GdC_{19}H_{31}O_8$, C, 41.9; H, 5.7%.

Infrared spectrometry (Nujol ν cm$^{-1}$): 1571(s), 1534(s), 1504 (s), 1450(m), 1351(s), 1226(m), 1135(s), 405(w).

Mass Spectrometry (EI$^+$): 544 [Gd(acac)$_3$(dme)]$^+$ (5%), 454[Gd(acac)$_3$]$^+$ (17%), 355 [Gd(acac)$_2$]$^+$ (16%), and lower mass ions.

37. TERBIUM TRIS-THD TETRAMETHYETHYLENEDIAMINE [Tb(thd)$_3$(tmeda)] —an example of a type I compound.

The first part of the preparation employs a similar method to example 1 to yield [Tb(thd)$_3$(H$_2$O)]$_n$. The [Tb(thd)$_3$(H$_2$O)]$_n$ (10.0 g, 13.8 mmole) is dissolved with warming in 60 ml of hexane, tmeda (3.2 ml, 27.6 mmole) is added and the solution stirred at room temperature for 1 hour. It is then stripped to an oil and set aside at 20° C. to crystallise.

Yield is 8.3 g, 72% of pink air stable crystals.

Melting point 98°–100° C.

Microanalysis Found: C, 57.0; H, 8.9. Calcd. TbC$_{39}$H$_{73}$O$_6$N$_2$, C, 56.8; H, 8.9%.

Freezing point depression in benzene yields a molecular weight of 805±37 (calc. 824).

38. TERBIUM TRIS-THD TRIGLYME [{Tb(thd)$_3$}$_2$(triglyme)]—an example of a type II compound.

The first part of the preparation employs a similar method to example 1 to yield [Tb(thd)$_3$(H$_2$O)]$_n$.

The [Tb(thd)$_3$(H$_2$O)]$_n$ (10.0 g, 13.8 mole) is dissolved with warming in 60 ml of hexane, triglyme (4.9 ml, 27.6 mmole) is added and the solution stirred at room temperature for 1 hour. It is then stripped to an oil and set aside at 20° C. to crystallise.

Yield is 13.3 g, 89% of pale-pink air stable crystals.

Melting point 86°–89° C.

Microanalysis Found: C, 55.3; H, 8.2. Calcd. Tb$_2$C$_{74}$H$_{132}$O$_{16}$, C, 55.7; H, 8.3%.

Infrared spectrometry (Nujol ν cm$^{-1}$): 1609(s), 1589(s), 1574(vs), 1536(s), 1505(s), 1452(m), 1422(m), 1388(s), 1359(vs), 1179(m), 1131(s), 474(m), 406(m).

Mass Spectrometry (EI$^+$): 708 [Tb(thd)$_3$]$^+$ (4%), 653 [Tb(thd)$_2$(Bu$^t$COCHCO]$^+$ (12%), 524 [Tb(thd)$_2$]$^+$ (9%) and lower mass ions.

Freezing point depression in benzene yields a molecular weight of 1555±83 (calc. 1594).

39. TERBIUM TRIS-TFA TETRAGLYME [{Tb(tfa)$_3$}$_2$(tetraglyme)]$_2$—an example of a type II compound.

The first part of the preparation employs a similar method to example 1 to yield [Tb(tfa)$_3$(H$_2$O)]$_n$. The [Tb(tfa)$_3$(H$_2$O)]$_n$ (5.0 g, 6.9 mole) is suspended in 200 ml of warm hexane, tetraglyme (3.1 ml, 13.8 mole) is added and the solution stirred at room temperature for 1 hour. It is then stripped to an oil and set aside at 20° C. to crystallise.

Yield is 4.2 g, 64% of pale-pink air stable crystals.

Melting point 83°–85° C.

Microanalysis Found: C, 33.0; H, 3.4. Calcd. Tb$_2$C$_{40}$H$_{46}$O$_{17}$F$_{18}$, C, 32.9; H, 3.2%.

Infrared spectrometry (Nujol ν cm$^{-1}$): 1583(s), 1571(s), 1532(m), 1504(s), 1357(s), 1280(m), 1226(m), 1182(s), 1137(s), 474(m), 405(w).

Mass Spectrometry (EI$^+$): 1083 [Tb$_2$(tfa)$_5$]$^+$ (2%), 618 [Tb(tfa)$_3$]$^+$ (9%), and lower mass ions.

40. DYSPROSIUM TRIS-ACAC TETRAGLYME [{Dy(acac)$_3$}$_2$(tetraglyme)]—an example of a type II compound.

The first part of the preparation employs a similar method to example 1 to yield [Dy(acac)$_3$(H$_2$O)$_2$]$_n$. The [Dy(acac)$_3$(H$_2$O)$_2$]$_n$ (3.0 g, 6.0 mole) is suspended in 60 ml of ethanol, tetraglyme (2.7 ml, 12 mole) is added and the solution stirred at room temperature for 1 hour. It is then stripped to an oil and set aside at 20° C. to crystallise.

Yield is 2.35 g, 41% of pale-yellow air stable crystals.

Melting point dissolves in the parent glyme, with no clear M. Pt.

Microanalysis Found: C, 42.5; H, 5.9. Calcd. Dy$_2$C$_{40}$H$_{64}$O$_{17}$, C, 42.1; H, 5.6%.

Infrared spectrometry (Nujol ν cm$^{-1}$): 1607(s), 1585(s), 1572(m), 1534(s), 1504(s), 1454(m), 1418(s), 1388(s), 1359(s), 1130(s), 474(m), 404(w).

Freezing point depression in benzene yields a molecular weight of 1115±42 (calc. 1141).

41. DYSPROSIUM TRIS-THD TRIGLYME [{Dy(thd)$_3$}$_2$(triglyme)]—an example of a type II compound.

The first part of the preparation employs a similar method to example 1 to yield [Dy(thd)$_3$(H$_2$O)]$_n$. The [Dy(thd)$_3$(H$_2$O)]$_n$ (2.5 g, 3.4 mmole) is dissolved with warming in 40 ml of hexane, triglyme (1.2 ml, 6.8 mmole) is added and the solution stirred at room temperature for 1 hour. It is then stripped to an oil and set aside at 20° C. to crystallise.

Yield is 3.2 g, 85% of pale-pink air stable crystals.

Melting point 85°–87° C.

Microanalysis Found: C, 55.7; H, 8.1. Calcd. Dy$_2$C$_{74}$H$_{132}$O$_{16}$, C, 55.5; H, 8.2%.

Infrared spectrometry (Nujol ν cm$^{-1}$): 1609(s), 1589(s), 1574(m), 1536(vs), 1504(s), 1452(s), 1422(m), 1388(s), 1359(vs), 1250(m), 1221(s), 1182(s), 1135(s), 404(w).

Freezing point depression in benzene yields a molecular weight of 1565±75 (calc. 1601).

Mass Spectrometry (EI$^+$): 708 [Dy(thd)$_3$]$^+$ (11%), 653 [Dy(thd)$_2$(Bu$^t$COCHCO]$^+$ (19%), 524 [Dy(thd)$_2$]$^+$ (3%) and lower mass ions.

42. DYSPROSIUM TRIS-THD HEPTAGLYME [{Dy(thd)$_3$}$_2$(heptaglyme)]—an example of a type II compound.

The first part of the preparation employs a similar method to example 1 to yield [Dy(thd)$_3$(H$_2$O)]$_n$. The [Dy(thd)$_3$(H$_2$O)]$_n$ (1.5 g, 2.1 mmole) is dissolved with warming in 20 ml of hexane, heptaglyme (1.46 ml, 4.1 mmole) is added and the solution stirred at room temperature for 1 hour. It is then stripped to an oil and set aside at 20° C. to crystallise.

Yield is 1.7 g, 76% of pale-yellow air stable crystals.

Melting point 67°–70° C.

Microanalysis Found: C, 55.8; H, 8.4. Calcd. Dy$_2$C$_{82}$H$_{148}$O$_{20}$, C, 55.4; H, 8.3%.

Infrared spectrometry (Nujol ν cm$^{-1}$): 1574(s), 1536(s), 1504 (vs), 1420(m), 1354(s), 1225(s), 1178(m), 1136(s), 474(w), 403(w).

Mass Spectrometry (EI$^+$): 1603 [Dy$_2$(thd)$_6$(triglyme)]$^+$ (0.5%), 1360 [Dy$_2$(thd)$_5$(Bu$^t$COCHCO)]$^+$ (3%), 1240 [Dy$_2$(thd)$_5$]$^+$ (17%), and lower mass ions.

43. HOLMIUM TRIS-THD TRIGLYME [{Ho(thd)$_3$}$_2$(triglyme)]—an example of a type II compound.

The first part of the preparation employs a similar method to example 1 to yield [Ho(thd)$_3$(H$_2$O)]$_n$. The

[Ho(thd)$_3$(H$_2$O)]$_n$ (2.5 g, 3.4 mmole) is dissolved with warming in 40 ml of hexane, triglyme (1.2 ml, 6.8 mmole) is added and the solution stirred at room temperature for 1 hour. It is then stripped to an oil and set aside at 20° C. to crystallise.

Yield is 2.9 g, 78% of pale-yellow air stable crystals.

Melting point 76°–78° C.

Microanalysis Found: C, 55.6; H, 8.4. Calcd. Ho$_2$C$_{74}$H$_{132}$O$_{16}$, C, 55.3; H, 8.2%.

Infrared spectrometry (Nujol ν cm$^{-1}$): 1608(s), 1588(s), 1574(m), 1535(vs), 1504(s), 1451(s), 1421(m), 1388(s), 1359(vs), 1252(m), 1220(s), 1180(s), 1134(s), 403(w).

Freezing point depression in benzene yields a molecular weight of 1550±70 (calc. 1606).

44. HOLMIUM TRIS-HFA TETRAGLYME [{Ho(hfa)$_3$}$_2$(tetraglyme)]—an example of a type II compound.

The preparation of Ho(hfa)$_3$(H$_2$O)]$_n$ is similar to the method used for example 1. The [Ho(hfa)$_3$(H$_2$O)]$_n$ (1.5 g, 1.9 mmole) was dissolved with warming in 20 ml of ethanol, tetraglyme (0.85 ml, 3.8 mole) is added and the solution stirred at room temperature for 1 hour. It is then stripped to an oil and set aside at 20° C. to crystallise.

Yield is 2.1 g 89%.

Melting point 72°–74° C.

Microanalysis Found: C, 27.0; H, 1.9. Calcd. Ho$_2$C$_{40}$H$_{28}$O$_{17}$F$_{36}$, C, 26.8; H, 1.57%.

Infrared spectrometry (Nujol ν cm$^{-1}$): 1572(s), 1531(s), 1502 (m), 1450(s), 1370(s), 1222(m), 1175(m), 1134(s), 403(w).

Mass Spectrometry (EI$^+$): 1365 [Ho$_2$(hfa)$_5$]$^+$ (9%), 786 [Ho(hfa)$_3$]$^+$ (24%), and lower mass ions due to hfa dissociation.

Freezing point depression in benzene yields a molecular weight of 1735±83 (calc. 1794).

45. HOLMIUM TRIS-TFA HEXAMETHYLTRIETHYLENETETRAAMINE [{Ho(tfa)$_3$}$_2$(hmteta)]—an example of a type II compound.

The preparation of Ho(tfa)$_3$(H$_2$O)]$_n$ is similar to the method used for example 1. The [Ho(tfa)$_3$(H$_2$O)]$_n$ (2.5 g, 3.9 mmole) was dissolved with warming in 30 ml of ethanol, hmteta (1.75 g, 7.8 mole) is added and the solution stirred at room temperature for 1 hour. It is then stripped to an oil and set aside at 20° C. to crystallise.

Yield is 3.2 g, 74% of pale-yellow air stable crystals.

Melting point 88°–92°.

Microanalysis Found: C, 34.4; H, 4.1. Calcd. Ho$_2$C$_{42}$H$_{54}$O$_{12}$F$_{18}$N$_4$, C, 34.1; H, 3.7%.

Mass Spectrometry (EI$^+$): 1095 [Ho$_2$(tfa)$_5$]$^+$ (5%), 624 [Ho(tfa)$_3$]$^+$ (64%) and lower mass ions containing tfa fragments.

46. ERBIUM TRIS-THD DIMETHOXYETHANE [Er(thd)$_3$(dme)]— an example of a type I compound.

The first part of the preparation employs a similar method to example 1 to yield [Er(thd)$_3$(H$_2$O)]$_n$. The [Er(thd)$_3$(H$_2$O)]$_n$ (6.0 g, 8.2 mmole) is dissolved with warming in 40 ml of hexane, diglyme (2.2 ml, 16.4 mmole) is added and the solution stirred at room temperature for 1 hour. It is then stripped to an oil and set aside at 20° C. to crystallise.

Yield is 6.7 g, 81% of pink air stable crystals.

Melting point: 94°–96° C.

Microanalysis Found: C, 55.0; H, 8.8. Calcd. ErC$_{37}$H$_{69}$O$_8$, C, 54.9; H, 8.5%.

Freezing point depression in benzene yields a molecular weight of 780±32 (calc. 808).

47. ERBIUM TRIS-THD DIGLYME [Er(thd)$_3$(diglyme)]$_2$—an example of a type III compound.

The first part of the preparation employs a similar method to example 1 to yield [Er(thd)$_3$(H$_2$O)]$_n$. The [Er(thd)$_3$(H$_2$O)]$_n$ (4.25 g, 5.8 mmole) is dissolved with warming in 40 ml of hexane, diglyme (1.56 ml, 11.6 mmole) is added and the solution stirred at room temperature for 1 hour. It is then stripped to an oil and set aside at 20° C. to crystallise.

Yield is 4.17 g, 83% of pink air stable crystals.

Melting point 72°–74° C.

Microanalysis Found: C, 28.1; H, 4.6. Calcd. ErC$_{39}$H$_{71}$O$_9$, C, 27.5; H, 4.2%.

Infrared spectrometry (Nujol ν cm$^{-1}$): 1576(vs), 1534(s), 1504(vs), 1455(vs), 1376(s), 1180(m), 1137(s), 473(m), 402(w).

Mass Spectrometry (EI$^+$): 717 [Er(thd)$_3$]$^+$ (37%), 656 [Er(thd)$_2$(Bu$^t$COCHCO)]$^+$ (26%), 534 [Er(thd)$_2$]$^+$ (100%) and lower mass ions.

48. ERBIUM TRIS-THD TRIGLYME [{Er(thd)$_3$}$_2$(triglyme)]—an example of a type II compound.

The first part of the preparation employs a similar method to example 1 to yield [Er(thd)$_3$(H$_2$O)]$_n$. The [Er(thd)$_3$(H$_2$O)]$_n$ (20 g, 27.2 mole) is dissolved with warming in 40 ml of hexane, triglyme (9.6 ml, 54.4 mmole) is added and the solution stirred at room temperature for 1 hour. It is then stripped to an oil and set aside at 20° C. to crystallise.

Yield is 17.4 g, 70% of pink air stable crystals.

Melting point 80°–82° C.

Microanalysis Found: C, 55.3; H, 8.3. Calcd. Er$_2$C$_{74}$H$_{132}$O$_{16}$, C, 55.1; H, 8.2%.

Infrared spectrometry (Nujol ν cm$^{-1}$): 1608(s), 1587(s), 1573(m), 1535(vs), 1505(s), 1453(s), 1422(m), 1386(s), 1358(vs), 1251(m), 1220(s), 1180(s), 1135(s), 405(w).

Freezing point depression in benzene yields a molecular weight of 1570±72 (calc. 1610).

Mass Spectrometry (EI$^+$): 711 [Er(thd)$_3$]$^+$ (11%), 656 [Er(thd)$_2$(Bu$^t$COCHCO)]$^+$ (19%), 527 [Er(thd)$_2$]$^+$ (3%) and lower mass ions.

49. THULIUM TRIS-THD TRIGLYME [{Tm(thd)$_3$}$_2$(triglyme)]—an example of a type II compound.

The first part of the preparation employs a similar method to example 1 to yield [Tm(thd)$_3$(H$_2$O)]$_n$. The [Tm(thd)$_3$(H$_2$O)]$_n$ (1.07 g, 1.45 mmole) is dissolved with warming in 20 ml of hexane, triglyme (0.6 ml, 2.9 mmole) is added and the solution stirred at room temperature for 1 hour. It is then stripped to an oil and set aside at 20° C. to crystallise.

Yield is 0.9 g, 77% of pale-green air stable crystals.

Melting point 65°–68° C.

Microanalysis Found: C, 55.1; H, 8.3. Calcd. Tm$_2$C$_{74}$H$_{132}$O$_{16}$, C, 55.0; H, 8.2%.

Infrared spectrometry (Nujol ν cm$^{-1}$): 1608(s), 1590(s), 1577(vs), 1538(vs), 1506(s), 1422(vs), 1359(v), 1286(w), 1246(w), 1226(m), 1180(m), 1140(sm), 404(w).

50. THULIUM TRIS-THD TETRAGLYME [{Tm(thd)$_3$}$_2$(tetraglyme)]—an example of a type II compound.

The first part of the preparation employs a similar method to example 1 to yield $[Tm(thd)_3(H_2O)]_n$. The $[Tm(thd)_3(H_2O)]_n$ (1.07 g, 1.45 mole) is dissolved with warming in 30 ml of hexane, tetraglyme (0.65 ml, 2.90 mmole) is added and the solution stirred at room temperature for 1 hour. The solvent was then removed and the resulting oil left to crystallise.

Yield is 1.10 g 63% of yellow-green air-stable crystals.
Melting point 71°–73° C.
Microanalysis Found: C, 55.4; H, 8.2. Calcd. $Tm_2C_{76}H_{136}O_{17}$, C, 55.0; H, 8.2%.
Infrared spectrometry (Nujol $\nu$ cm$^{-1}$): 1589(s), 1575(s), 1538(s), 1505 (s), 1359(s), 1181(m), 1139(s), 475(mw), 406(w).
Freezing point depression in benzene yields a molecular weight of 1590±84 (calc. 1658).
Mass Spectrometry (EI$^+$): 719 $[Tm(thd)_3]^+$ (7%), 662 $[Tm(thd)_2(Bu^tCOCHCO)]^+$ (42%), 536 $[Tm(thd)_2]^+$ (87%) and lower mass ions.

51. THULIUM TRIS-ACAC HEPTAGLYME [{Tm(acac)_3}_2(heptaglyme)]—an example of a type II compound.

The preparation of $[Tm(acac)_3]_n$ is similar to the method used for example 3. The quantities used are $[Tm(hmdz)_3]_n$ (2 g, 3.1 mole), acacH (0.93 ml, 9.3 mole) and heptaglyme (2.2 ml, 6.2 mmole). The solution is stirred at room temperature for 1 hour and then stripped to an oil and set aside at 20° C. to crystallise.

Yield is 2.5 g, 62% of yellow air stable crystals.
Melting point: 83°–85° C.
Microanalysis Found: C, 43.2; H, 6.0. Calcd. $Tm_2C_{46}H_{76}O_{20}$, C, 42.9; H, 5.9%.
Mass Spectrometry (EI$^+$): 1286 $[Tm_2(acac)_6(heptaglyme)]^+$ (0.3%), 833 $[Tm_2(acac)_5]^+$ (42%), 466 $[Tm(acac)_3]^+$ (24%) and lower mass ions.

52. YTTERBIUM TRIS-Ph$_2$CAC PENTAMETHYLDIETHYLENETRIAMINE [Yb(Ph$_2$acac)$_3$(pmdeta)]—an example of a type I compound.

The first part of the preparation employs a similar method to example 3, to yield $[Yb(Ph_2acac)_3]_n$. The $[Yb(acac)_3]_n$ (2.0 g, 4.25 mole) is suspended in 50 ml of chloroform, pmdeta (1.5 ml, 8.5 mole) is added and the solution stirred at room temperature for 1 hour. It is then stripped to an oil and set aside at 20° C. to crystallise.

Yield is 3.2 g, 92% of colourless air stable crystals.
Melting point 126°–130° C.
Microanalysis Found: C, 64.2; H, 5.8. Calcd. $YbC_{54}H_{56}O_6N_3$, C, 63.8; H, 5.5%.
Mass Spectrometry (EI$^+$): 1016 $[Yb(Ph_2acac)_3(pmdeta)]^+$ (19%), 842 $[Yb(Ph_2acac)_3]^+$ (7%) and lower mass species.

53. YTTERBIUM TRIS-THD DIGLYME [Yb(thd)$_3$(diglyme)]— an example of a type I compound.

The first part of the preparation employs a similar method to example 1 to yield $[Yb(thd)_3(H_2O)]_n$. The $[Yb(thd)_3(H_2O)]_n$ (0.8 g, 1.22 mmole) is dissolved with warming in 10 ml of hexane, diglyme (0.34 ml, 2.5 mmole) is added and the solution stirred at room temperature for 1 hour. It is then stripped to an oil and set aside at 20° C. to crystallise.

Yield is 0.74 g, 76% of colourless air stable crystals.
Melting point 72°–74° C.
Microanalysis Found: C, 55.1; H, 8.6. Calcd. $YbC_{39}H_{71}O_9$, C, 54.7; H, 8.3%.

Infrared spectrometry (Nujol $\nu$ cm$^{-1}$): 1576(vs), 1534(s), 1504(vs), 1455(vs), 1376(s), 1180(m), 1137(s), 473(m), 402(w).
Mass Spectrometry (EI$^+$): 717 $[Er(thd)_3]^+$ (37%), 656 $[Er(thd)_2(Bu^tCOCHCO)]^+$ (26%), 534 $[Er(thd)_2]^+$ (100%) and lower mass ions.

54. YTTERBIUM TRIS-THD TRIGLYME [{Yb(thd)_3}_2(triglyme)]—an example of a type II compound.

The first part of the preparation employs a similar method to example 1 to yield $[Yb(thd)_3(H_2O)]_n$. The $[Yb(thd)_3(H_2O)]_n$ (0.8 g, 1.22 mmole) is dissolved with warming in 20 ml of hexane, diglyme (0.34 ml, 2.5 mmole) is added and the solution stirred at room temperature for 1 hour. It is then stripped to an oil and set aside at 20° C. to crystallise.

Yield is 0.73 g, 66% of air stable crystals.
Melting point 68°–70° C.
Microanalysis Found: C, 54.8; H, 8.3. Calcd. $Yb_2C_{74}H_{132}O_{16}$, C, 54.7; H, 8.1%.
Infrared spectrometry (Nujol $\nu$ cm$^{-1}$): 1607(s), 1590(s), 1577(vs), 1538(vs), 1506(s), 1423(vs), 1359(vs), 1288(w), 1245(w), 1222(m), 1181(m), 1136(s), 404(w).
Freezing point depression in benzene yields a molecular weight of 1670±72 (calc. 1712).

We claim:

1. A rare earth compound of formula $$[(ML_3)_xA]_y$$

where M represents one or more metals chosen from the rare earth metals and yttrium, L is a bidentate ligand, A is a polyether, polyamine or polyether-amine, and x and y are each 1 or 2 but are not both 2.

2. A compound according to claim 1 wherein L contains a ligand group of formula

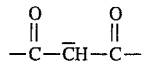

3. A compound according to claim 1 wherein L is a β-diketone ligand.

4. A compound according to claim 1 wherein the ligand L is a radical of a compound selected from the group consisting of acetylacetone, tetramethylheptanedione, trifluoroacetylacetone, hexafluoroacetylacetone, and 1,5-diphenylpentanedione.

5. A compound according to claim 1 wherein A is derived from a polyether of formula:

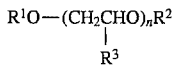

wherein $R^1$, $R^2$ and $R^3$ are each hydrogen or alkyl of 1 to 4 carbon atoms, and n is from 1 to 10, and/or from a polyamine of formula:

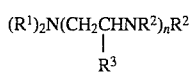

wherein $R^1$, $R^2$ and $R^3$ and n are as hereinbefore defined.

6. A compound according to claim 5 wherein A is derived from a said polyether wherein $R^1$ and $R^2$ are each alkyl of 1 to 4 carbon atoms, $R^3$ is hydrogen, and n is an integer from 1 to 7.

7. A compound according to claim 5 wherein A is a radical of a compound selected from the group consisting of monoglyme, diglyme, triglyme, tetraglyme, and heptaglyme.

8. A compound according to claim 5 wherein A is derived from a said polyamine wherein $R^1$ and $R^2$ are each alkyl of 1 to 4 carbon atoms, $R^3$ is hydrogen, and n is an integer from 1 to 3.

9. A compound according to claim 5 wherein A is a radical of a compound selected from the group consisting of tmeda, pmdeta, and hmteta.

10. A compound according to claim 1 where L is a radical of a compound selected from the group consisting of acetylacetone, tetramethylheptanedione, or diphenylacetylacetone, A is a radical of a compound selected from the group consisting of monoglyme, tetraglyme, tmeda, and pmdeta, x=1 and y=1.

11. A compound according to claim 1 wherein L is a radical of a compound selected from the group consisting of acetylacetone, tetramethylheptanedione, trifluoroacetlacetone, hexafluoroacetylacetone, or diphenylacetylacetone, A is a radical of a compound selected from the group consisting of triglyme, tetraglyme, heptaglyme, or hmteta, x=2 and y=1.

12. A compound according to claim 1 wherein L is derived from tetramethylheptanedione or hexafluoroacetylacetone, A is derived from diglyme, x=1 and y=2.

13. A compound according to claim 1 wherein M is selected from the group consisting of yttrium, a combination of yttrium with europium or terbium, lanthanum, a combination of lanthanum and thulium, cerium, praseodymium, neodymium, samarium, europium, gadolinium, terbium, dysprosium, holmium, erbium, thulium, or ytterbium.

14. A compound according to claim 1 having a molecular weight less than 1000 per metal atom.

* * * * *